United States Patent
Liang et al.

(10) Patent No.: US 9,176,252 B2
(45) Date of Patent: Nov. 3, 2015

(54) ESTIMATING PETROPHYSICAL PARAMETERS AND INVASION PROFILE USING JOINT INDUCTION AND PRESSURE DATA INVERSION APPROACH

(75) Inventors: Lin Liang, Cambridge, MA (US); Aria Abubakar, North Reading, MA (US); Tarek Habashy, Burlington, MA (US); Michael Thambynayagam, Sugar Land, TX (US)

(73) Assignee: Schlumberger Technology Corporation, Cambridge, MA (US)

( * ) Notice: Subject to any disclaimer, the term of this patent is extended or adjusted under 35 U.S.C. 154(b) by 840 days.

(21) Appl. No.: 12/607,708

(22) Filed: Oct. 28, 2009

(65) Prior Publication Data

US 2010/0185393 A1   Jul. 22, 2010

Related U.S. Application Data

(60) Provisional application No. 61/145,658, filed on Jan. 19, 2009.

(51) Int. Cl.
   *G01F 25/00* (2006.01)
   *G01V 3/38* (2006.01)
   *G01V 3/28* (2006.01)

(52) U.S. Cl.
   CPC ... *G01V 3/38* (2013.01); *G01V 3/28* (2013.01)

(58) Field of Classification Search
   USPC .............................................................. 702/7
   See application file for complete search history.

(56) References Cited

U.S. PATENT DOCUMENTS

| 5,663,499 A | 9/1997 | Semmelbeck et al. |
| 2007/0256489 A1 | 11/2007 | Wu et al. |
| 2009/0150124 A1* | 6/2009 | Wilt et al. .......................... 703/1 |

FOREIGN PATENT DOCUMENTS

CA    2401940 A1    9/2002

OTHER PUBLICATIONS

David Allen, Invasion Revisited, Oilfield Review, Jul. 1991, p. 10-23.*
David Allen, Invasion Revisited, Oilfield Review, Jul. 1991, p. 10-23. [retrieved on Feb. 23, 2015]. Online, Retrieved from the Internet:< URL: http://www.slb.com/~/media/Files/resources/oilfield_review/ors91/jul91/3_invasion.pdf.*
An Introduction to Geophysical Exploration, Third Edition, Philip Kearey, printed Jun. 17, 2015, 281 pages.*
International Search Report of PCT Application No. PCT/US2010/021161 dated Sep. 7, 2010.

(Continued)

*Primary Examiner* — Tung S Lau
(74) *Attorney, Agent, or Firm* — Jakub M. Michna

(57) ABSTRACT

Methods and related systems are described relating to an inversion approach for interpreting the geophysical electromagnetic data. The inversion can be constrained by using a multiphase fluid flow simulator (incorporating pressure data if available) which simulates the fluid flow process and calculates the spatial distribution of the water saturation and the salt concentration, which are in turn transformed into the formation conductivity using a resistivity-saturation formula. In this way, the inverted invasion profile is consistent with the fluid flow physics and moreover accounts for gravity segregation effects. Jointly with the pressure data, the inversion estimates a parametric one-dimensional distribution of permeability and porosity. The fluid flow volume is directly inverted from the fluid-flow-constrained inversion of the electromagnetic data.

23 Claims, 17 Drawing Sheets

(56) References Cited

OTHER PUBLICATIONS

Abubakar et al., "Nonlinear Inversion in Electrode Logging in a Highly Deviated Formation with Invasion Using an Oblique Coordinate System," IEEE Transactions on Geoscience and Remote Sensing, Jan. 2000, vol. 38(1): pp. 25-38.

Abubakar et al., "Chapter 12: Application of a Non-orthogonal Coordinate System to the Inverse Single-Well Electromagnetic Logging Problem," Three Dimensional Electromagnetics, Eds. Ahdanov et al., 2002: pp. 215-231.

Abubakar et al., "A 3D parametric inversion algorithm for triaxial induction data," Geophysics, Jan.-Feb. 2006, vol. 71(1): pp. G1-G9.

Abubakar et al., "An Enhanced Gauss-Newton Inversion Algorithm Using a Dual-Optimal Grid Approach," IEEE Transactions on Geoscience and Remote Sensing, Jun. 2006, vol. 44(6): pp. 1419-1427.

Abubakar et al., "Three-Dimensional Single-Well Imaging of the Multi-Array Triaxial Induction Logging Data," SEG/New Orleans Annual Meeting, SEG Technical Program Expanded Abstracts, 2006, vol. 25: pp. 411-415.

Alpak et al., "Joint Inversion of Transient-Pressure and Time-Lapse Electromagnetic Logging Measurements," Petrophysics, May-Jun. 2004, vol. 45(3): pp. 251-267.

Alpak et al., "Joint inversion of transient pressure and dc resistivity measurements acquired with in-situ permanent sensors: A numerical study," Geophysics, Sep.-Oct. 2004, vol. 69(5): pp. 1173-1191.

Alpak et al., "Petrophysical inversion of borehole array-induction logs: Part 1—Numerical examples," Geophysics, Jul.-Aug. 2006, vol. 71(4): pp. F101-F119.

Alpak et al., "SPE 90960: Simultaneous Estimation of In-Situ Multi-Phase Petrophysical Properties of Rock Formations from Wireline Formation Tester and Induction Logging Measurements," SPE International, 2004: pp. 1-17.

Alumbaugh et al., "A Numerical Sensitivity Study of Three Dimensional Imaging From a Single Borehole," Petrophysics, Jan.-Feb. 2001, vol. 42(1): pp. 19-31.

Angeles et al., "Advantages in Joint-Inversions of Resistivity and Formation-Tester Measurements: Examples from a Norwegian Field," SPWLA 49th Annual Logging Symposium, May 2008: pp. 1-16.

Archie, "The Electrical Resistivity Log as an Aid in Determining Some Reservoir Characteristics," Transactions of the AIME, Dec. 1942, vol. 146(1): pp. 54-62.

Barber et al., "SPE 90526: Determining Formation Resistivity Anisotropy in the Presence of Invation," SPE International, 2004: pp. 1-25.

Dennis et al., "Chapter 5: Newton's Method for Nonlinear Equations and Unconstrained Minimization," Nonlinear Equations and Unconstrained Optimization, Prentice Hall, Inc.: New Jersey, 1983: pp. 86-110.

Dewan et al., "Mudcake Buildup and Invasion in Low Permeability formations; Application to Permeability Determination by Measurement While Drilling," SPWLA 34th Annual Logging Symposium, Jun. 1993: pp. 1-24.

Druskin et al., "New spectral Lanczos decomposition method for induction modeling in arbitrary 3-D geometry," Geophysics, May-Jun. 1999, vol. 64(3): pp. 701-706.

Epov et al., "Time Evolution of the Near Borehole Zone in Sandstone Reservoir through the Time-Lapse Data of High-Frequency Electromagnetic Logging," SPWLA 43rd Annual Logging Symposium, Jun. 2002: pp. 1-10.

Ferguson et al., "Filtration from Mud During Drilling," Journal of Petroleum Technology, Feb. 1954, vol. 6(2): pp. 30-43.

Habashy et al., "A General Framework for Constraint Minimization for the Inversion of Electromagnetic Measurements," Progress in Electromagnetics Research, PIER, 2004, vol. 46: pp. 265-312.

Horner, "Pressure Build-Up in Wells," Proceedings Third World Petroleum Congress—Section II, May-Jun. 1951: pp. 503-521.

Kuchuk et al., "SPE 116068: Determination of In-Situ Two-Phase Flow Properties Through Downhole Fluid Movement Monitoring," SPE International, 2008: pp. 1-23.

Moran et al., "Theoretical Analysis of Pressure Phenomena Associated with the Wireline Formation Tester," Journal of Petroleum Technology, Aug. 1963, vol. 14(8): pp. 899-908.

Moskow et al., "A Finite Difference Scheme for Elliptic Equations with Rough Coefficients Using a Cartesian Grid Nonconforming to Interfaces," Siam J. Numer. Anal., 1999, vol. 36(2): pp. 442-464.

Pereira et al., "Estimation of Permeability and Permeability Anisotropy in Horizopntal Wells Through Numerical Simulation of Mud Filtrate Invasion," Rio Oil & Gas Expo and Conference, 2008: pp. 1-10.

Ramakrishnan et al., "Formation producibility and fractional flow curves from radial resistivity variation caused by drilling fluid invasion," Phys. Fluids, Apr. 1997, vol. 9(4): pp. 833-844.

Ramakrishnan et al., "Water-Cut and Fractional-Flow Logs from Array-Induction Measurements," SPE Reservoir Eval. & Eng., Feb. 1999, vol. 2(1): pp. 85-94.

Salazar et al., "Estimation of Permeability from Borehole Array Induction Measurements: Application to the Petrophysical Appraisal of Tight Gas Sands," Petrophysics, Dec. 2006, vol. 47(6): pp. 527-544.

Semmelbeck et al., "The Effects of Mud-Filtrate Invasion on the Interpretation of Induction Logs," SPE Formation Evaluation, Jun. 1988, vol. 3(2): pp. 386-392.

Semmelbeck et al., "SPE 30581: Invasion-Based Method for Estimating Permeability from Logs," SPE International, 1995: pp. 1-15.

Tobola et al., "SPE19606: Determination of Reservoir Permeability from Repeated Induction Logging," SPE Formation Evaluation, Mar. 1991: pp. 20-26.

Torres-Verdin et al., "Petrophysical inversion of borehole array-induction logs: Part II—Field data examples," Geophysics, Sep.-Oct. 2006, vol. 71(5): pp. G261-G268.

Williams et al., "Evaluation of Filtration Properties of Drilling Mud," Drilling and Production Practice, 1938: pp. 20-28.

Wu et al., "The Influence of Water-Base Mud Properties and Petrophysical Parameters on Mudcake Growth, Filtrate Invasion, and Formation Pressure," Petrophysics, Feb. 2005, vol. 46(1): pp. 14-32.

Yao et al., "Reservoir Permeability Estimation from Time-Lapse Log Data," SPE Formation Evaluation, Jun. 1996: pp. 69-74.

Yee, Numerical Solution of Initial Boundary Value Problems Involving Maxwell's Equations in Isotropic Media, IEEE Transactions on Antennas and Propagation, May 1966, vol. A-14(3): pp. 302-307.

Salamy et al., "SPE 71568: Estimating Multiphase Flow Properties Using Pressure and Flowline Water-Cut Data from Dual Packer Formation Tester Interval Tests and Openhole Array Resistivity Measurements," SPE International, 2001: pp. 1-8.

Zhang et al., "Estimation of True Formation Resistivity and Water Saturation with a time-Lapse Induction Logging Method," The Log Analyst, Mar.-Apr. 1999, vol. 40(2): pp. 138-148.

* cited by examiner

418

420

ESTIMATING PETROPHYSICAL PARAMETERS AND INVASION PROFILE USING JOINT INDUCTION AND PRESSURE DATA INVERSION APPROACH

CROSS REFERENCE TO RELATED APPLICATION

This patent application claims benefit of U.S. Provisional Patent Application Ser. No. 61/145,658, filed Jan. 19, 2009, which is incorporated by reference herein.

FIELD OF THE INVENTION

This invention relates broadly to the investigation of geological formations traversed by a borehole. More particularly, this invention relates to a method for integrating electromagnetics and multi-phase fluid flow in order to provide a robust, physically consistent interpretation for reservoir characterization.

BACKGROUND OF THE INVENTION

Induction logging measurements are sensitive to water saturation and brine concentration in the rock pores. In an active reservoir, the formation's petrophysical parameters can have a strong imprint on the temporal and spatial distribution of water saturation and salt concentration, which in turn can be transformed into the distribution of formation conductivity using an appropriate saturation-resistivity equation. This relationship between induction measurements and the petrophysical parameters offers an opportunity to integrate electromagnetics and multi-phase fluid flow to provide a robust, physically consistent interpretation for reservoir characterization.

Induction logging tools can be used to determine the formation resistivity and invasion profile via a model-based inversion approach. See, Habashy, T. M. and A. Abubakar, 2004, A general framework for constraint minimization for the inversion of electromagnetic measurements: Progress In Electromagnetics Research, 46, 265-312 (hereinafter "Habashy and Abubakar"); Barber, T., B. Anderson, A. Abubakar, T. Broussard, K. Chen, S. Davydycheva, V. Druskin, T. Habashy, D. Homan, G. Minerbo, R. Rosthal, R. Schlein, and H. Wang, 2004, Determining formation resisitvty anisotropy in the presence of invasion, in SPE Annual Technical Conference and Exhibition, paper 90526; Abubakar, A., T. M. Habashy, V. Druskin, L. Knizhnerman, and S. Davydycheva, 2006, A 3d parametric inversion algorithm for triaxial induction data: Geophysics, 71, G1-G9; and Abubakar, A., T. M. Habashy, V. Druskin, and L. Knizhnerman, 2006, An enhanced gauss-newton inversion algorithm using a dual-optimal grid approach: IEEE Transactions on Geoscience and Remote Sensing, 44, 1419-1427. However, this application is constrained by some simplifying assumptions, for example, assuming a well penetrating a layer-cake formation with a step-profile three-parameter ($R_{xo}$, $R_t$, $D_i$) invasion model. The quality and accuracy of the inversion results are affected by the complexity of the reservoir configuration and the actual invasion profile. In horizontal or highly deviated wells or in anisotropic formations, invasion profiles become too complex to be described by a simple invasion model. An alternative inversion approach is to employ the so-called pixel-based inversion method. See: Abubakar, A. and P. M. van den Berg, 2000, Nonlinear inversion in electrode logging in a highly deviated formation with invasion using an oblique coordinate system: IEEE Transactions on Geoscience and Remote Sensing, 38, 25-38; Alumbaugh, D. and M. Wilt, 2001, A numerical sensitivity study of three-dimensional imaging from a single borehole: Petrophysics, 42, 19-31; Abubakar, A. and P. van den Berg, 2002, Application of a non-orthogonal coordinate system to inverse single-well electromagnetic logging problem: Three-Dimensional Electromagnetics, eds. M. S. Zhdanov and P. E. Wannamaker, 215-231; Abubakar, A. and T. Habashy, 2006, Three-dimensional single-well imaging of the multi-array triaxial induction logging data, in SEG Technical Program Expanded Abstracts, volume 25, 411-415. A disadvantage of this pixel-based inversion method is that the number of unknowns used to describe the configuration is large and hence, a large number of unknown model parameters often need to be inverted. This approach will only provide a qualitative inverted resistivity map (an image) around the wellbore.

On the other hand, the mud-filtrate invasion affects the interpretation of well testing or wireline formation test. Although some researchers studied and discussed the influence of invasion to the formation test interpretation, practically, the interpretation of formation test usually still employs a single-phase fluid flow model regardless of the mud-filtrate invasion. The error associates with this can be neglected only when the mobility of the mud-filtrate is very close to that of the formation fluid and the capillary pressure is negligible or the invaded mud-filtrate has already been cleaned up from the test target zone by a drawdown, which may be time-consuming. A more realistic invasion profile will benefit both induction data interpretation and formation test interpretation.

Some previous works have already exploited the benefit of integrating the electromagnetic model with the multiphase fluid flow model. In Semmelbeck, M. E. and S. A. Holditch, 1988, The effects of mud-filtrate invasion on the interpretation of induction logs: SPE (hereinafter "Semmelbeck and Holditch (1988)"), an attempt is made to develop a model to simulate the mud-filtrate invasion process, which deals with the mud-cake and the formation simultaneously, and incorporated the capability to simulate the salt transport to calculate the formation resistivity. This model was then used to analyze the effect of the mud-cake permeability, the formation permeability, the porosity and the overbalance pressure on the induction logging data. In Tobola, D. P. and S. A. Holditch, 1991, Determination of reservoir permeability from repeated induction logging: SPE Formation Evaluation, 20-26 (hereinafter "Tobola and Holditch (1991)"), the approach described in Semmelbeck and Holditch (1988) was applied to a low permeability reservoir and determined the reservoir permeability by history matching the change in the induction logging data over time. The effect of the initial water saturation on the induction logging data was also analyzed. In this approach, the mud-cake permeability profile over time must be accurately simulated to properly interpret the induction logging data. In Yao, C. Y. and S. A. Holditch, 1996, Reservoir permeability estimation from time-lapse log data: SPE Formation Evaluation, 69-74 (hereinafter "Yao and Holditch (1996)"), the approach described in Semmelbeck and Holditch (1988) was extended to history match both the time-lapse resistivity and neutron logging data. This technique was used to estimate the reservoir permeability, which was verified against production data and core analysis.

The approaches described in Semmelbeck and Holditch (1988), Tobola and Holditch (1991) and Yao and Holditch (1996) simulate the mud-filtrate invasion assuming a mud-cake with a constant thickness and a variable permeability, which need to be accurately determined from other independent measurement data. See: Ferguson, C. K. and J. A. Klotz, 1954, Filtration from mud during drilling: Trans., AIME 201, 29-42; and Williams, M. and G. E. Cannon, 1938, Evaluation of filtration properties of drilling muds: The Oil Weekly, 25-32. These approaches ignore gravity and diffusion effects, and aim to estimate the permeability in tight formations. However, this estimation heavily depends on the precision of determining mud-cake properties, which is another difficult problem to be resolved.

Semmelbeck, M. E., J. T. Dewan, and S. A. Holditch, 1995, Invasion-based method for estimating permeability from logs: SPE 30581 presented at the 1995 SPE Annual Technical Conference and Exhibition, Dallas, 22-25 describes an extension of their previous work to integrate the fluid flow model with the Dewan's mudcake growth model, which is an experimentally-verified model for predicting the mud-cake thickness and the permeability during static and dynamic filtration conditions. See: Dewan, J. T. and M. E. Chenevert, 1993, Mudcake buildup and invasion in low permeability formations: application to permeability determination by measurement while drilling: SPWLA 34th Annual Logging Symposium, 13-16. This approach was applied to the new generation of array induction logging data. From a linear covariance analysis, they concluded that their method could provide reasonable estimates of the permeability in low to moderate permeable formations, but the method could not provide accurate estimates of the saturation-dependent properties.

Ramakrishnan, T. S. and D. J. Wilkinson, 1997, Formation producibility and fractional flow curves from radial resistivity variation caused by drilling fluid invasion: Physics of Fluids, 9, 833-844, and Ramakrishnan, T. S. and D. J. Wilkinson, Water-cut and fractional flow logs from array-induction measurements: SPE Reservoir Evaluation & Engineering, 2, 85-94 discuss establishing a mathematical model to estimate the fractional flow and the relative permeability curves from the array induction logging measurements. Based on the work described in the two Ramakrishnan papers, Zeybek, M., T. Ramakrishnan, S. Al-Otaibi, S. Salamy, and F. Kuchuk, 2001, Estimating multiphase flow properties using pressure and flowline water-cut data from dual packer formation tester interval tests and openhole array resistivity measurements: SPE 71568 discusses a methodology for estimating the horizontal and vertical layer permeabilities and the relative permeabilities using array induction logging tool measurements, pressure transient measurements and water-cut measurements from a packer-probe wireline formation tester. This joint inversion was done in a sequential mode. In this method, fractional flow parameters (connate water saturation, residual water saturation, maximum residual oil saturation, filtrate loss and pore size distribution) are estimated by matching resistivity measurements. These estimated fractional flow parameters are then input into a numerical model for the sampling process to ultimately match the observed and simulated water cut and pressure data. The final outputs are the relative, the horizontal and vertical permeabilities.

Alpak, F. O., T. M. Habashy, C. Torres-Verdin, and V. Dussan, 2004, Joint inversion of pressure and time-lapse electromagnetic logging measurements: Petrophysics, 45, 251-267 (hereinafter "Alpak, et al. (2004)"); Alpak, F. O., C. Torres-Verdin, and T. M. Habashy, 2004, Joint inversion of pressure and dc resistivity measurements acquired with in-situ permanent sensors: a numerical study: Geophysics, 69, 1173-1191; Alpak, F. O., C. Torres-Verdin, and T. M. Habashy 2006, Petrophysical inversion of borehole array-induction logs: Part I-numerical examples: Geophysics, 71, F101-F119; and Alpak, F. O., C. Torres-Verdin, T. M. Habashy, and K. Sephernoori, 2004, Simultaneous estimation of in-situ multiphase petrophysical properties of rock formations from wireline formation tester and induction logging measurements: SPE 90960 all discuss the simultaneous estimation of in-situ multiphase petrophysical properties of rock formations from wireline formation tester and induction logging measurements. The papers also discuss extensive work to assess the sensitivity of array induction measurements to the presence of the water-based mud-filtrate invasion for various combinations of petrophysical parameters and fluid properties. Torres-Verdin, C., F. O. Alpak, and T. M. Habashy, 2006, Petrophysical inversion of borehole array-induction log: Part II-field data examples: Geophysics, 71, G261-G268; and Salazar, J. M., C. Torres-Verdin, F. O. Alpak, T. M. Habashy, and J. D. Klein, 2006, Estimation of permeability from borehole array induction measurements: Application to the petrophysical appraisal of tight gas sands: Petrophysics, 47, 527-544 discuss applying method described by Alpak to some low or moderate permeability gas reservoirs for estimating the permeability and the porosity. This method employs a modified UTCHEM code (INVADE) (see Wu, J., C. Torres-Verdin, K. Sepehrnoori, and M. Proett, 2005, The influence of water-base mud properties and petrophysical parameters on mudcake growth, filtrate invasion, and formation pressure: Petrophysics, 46, 14-32) to calculate the time-dependent mud-filtrate loss rate, and takes the average of this rate as the injection rate to run a two-phase three-component fluid flow model for simulating the mud-filtrate invasion process, which consequently affects the resistivity measurements. Therefore, the accuracy of the inverted petrophysical parameters can depend on the mud-filtrate loss calculation, which is still a difficult problem at present. Angeles, R., J. Skolnakorn, F. Antonsen, A. Chandler, and C. Torres-Verdin, 2008, Advantages in joint-inversions of resistivity and formation-tester measurements: Examples from a norwegian field: SPWLA 49th Annual Logging Symposium, Edinburgh, Scotland discusses advancing previous work by using a reservoir simulator dynamically-coupled to a mud-filtrate invasion model. Hence they integrated the calculation of mud-filtrate invasion rate into the inversion process.

Pereira, N., R. Altman, J. Rasmus, and J. Oliveira, 2008, Estimation of permeability and permeability anisotropy in horizontal wells through numerical simulation of mud filtrate invasion: Rio Oil & Gas Expo and Conference, Rio de Janeiro. discusses an approach to estimate formation permeability and permeability anisotropy using dual inversion of time-lapse azimuthal laterolog-while-drilling and near well-bore numerical simulation of the water-based mud-filtrate invasion. This method requires a priori bottom hole pressure while drilling and assumes a known constant mud-cake permeability. Kuchuk, F., L. Zhan, S. M. Ma, A. M. Al-Shahri, T. S. Ramakrishnan, B. Altundas, M. Zeybek, R. Loubens, and N. Chugunov, 2008, Determination of in-situ two-phase flow properties through downhole fluid movement monitoring: SPE 116068 presented at the 2008 SPE Annual Technical Conference and Exhibition held in Denver, Colo., USA, 21-24 discusses method for in-situ estimation of two-phase transport properties of porous media using the time-lapse DC resistivity data, pressure and flow rate data. The time-lapse DC resistivity are recorded using a permanent downhole electrode resistivity array. The pressure and flow rate data are obtained from the injection test regardless of the mud-filtrate invasion. The integrated interpretation is based on an inversion workflow, which employs a multi-layered integrated flow/electrical numerical simulator to solve the fluid flow, the salt transport and the DC electrical array response. A field experiment conducted in a carbonate reservoir has been used to verify the proposed method.

Most of the above works involve the simulation of the mud-filtrate invasion process to obtain the invasion rates as accurately as possible. However, the mud-filtrate invasion is a dynamic and complex process. It starts with a high invasion rate, which is mainly controlled by the overbalance pressure and the formation permeability when a well is drilled. After the mud-cake is formed, the invasion rate will tend to be controlled by the mud-cake since the permeability of mud-cake is normally much lower than that of the formation. There have been extensive works on the simulation of the mud-filtrate invasion process, which although possible, is still too complex for any practical application, especially when considering the complicated drilling and reaming conditions, such as the mud circulation rate, workover, mud-cake scraped by the tools, and so on.

SUMMARY OF THE INVENTION

This method according to some embodiments of the invention paper includes the general framework developed in Alpak et al. (2004). However, the method of the invention propose to directly invert the average mud-filtrate invasion rates for each flow unit or each depth interval, in order to avoid using complicated, time-consuming mud-cake growth and invasion models. Moreover, based on the derived invasion profile, the joint inversion technique according to some embodiments of the invention also provide a more reliable interpretation of formation test compared to the conventional methods. The method according to the invention can be applied to support horizontal and deviated wells with dipping formation layers.

According to some embodiments, a method of estimating fluid invasion rate for portions of a subterranean formation of interest surrounding a borehole is provided. The method includes receiving electromagnetic survey data of the subterranean formation of interest and receiving fluid flow characteristics relating to the formation of interest. A direct inversion is performed of the electromagnetic data and constrained by the fluid flow simulator for a fluid invasion rate, and the fluid invasion rate is thereby estimated based. The fluid can be borehole originating fluids such as mud filtrate or completion fluids. The fluid flow simulator can also be used to generate the pressure transient data made in the borehole. If the pressure transient measurements are available to be compared with the one generated from the fluid flow simulator then permeability can be estimated. According to some embodiments porosity is also estimated based on the inversion. A quantitative predictive formation model can be generated based on the inversion. The electromagnetic data can be obtained using various tools operated in a single well. The same or similar workflow or process can be applied to different configurations such as cross-well, surface to borehole, borehole to surface and surface to surface.

According to some embodiments, a method of estimating porosity for a subterranean formation of interest including one or more geologic beds is provided. The method includes receiving electromagnetic survey data and fluid flow characteristics of the formation of interest, and estimating porosity within at least a portion of the formation of interest based at least in part on the electromagnetic survey data and the fluid flow characteristics. The estimation has a spatial resolution such that at least two porosity values are estimated for each of the one or more geologic beds.

According to some embodiments, systems are provided for estimating fluid invasion rate and for estimating porosity for portions of a subterranean formation of interest surrounding a borehole.

Additional objects and advantages of the invention will become apparent to those skilled in the art upon reference to the detailed description taken in conjunction with the provided figures.

Figure 1:
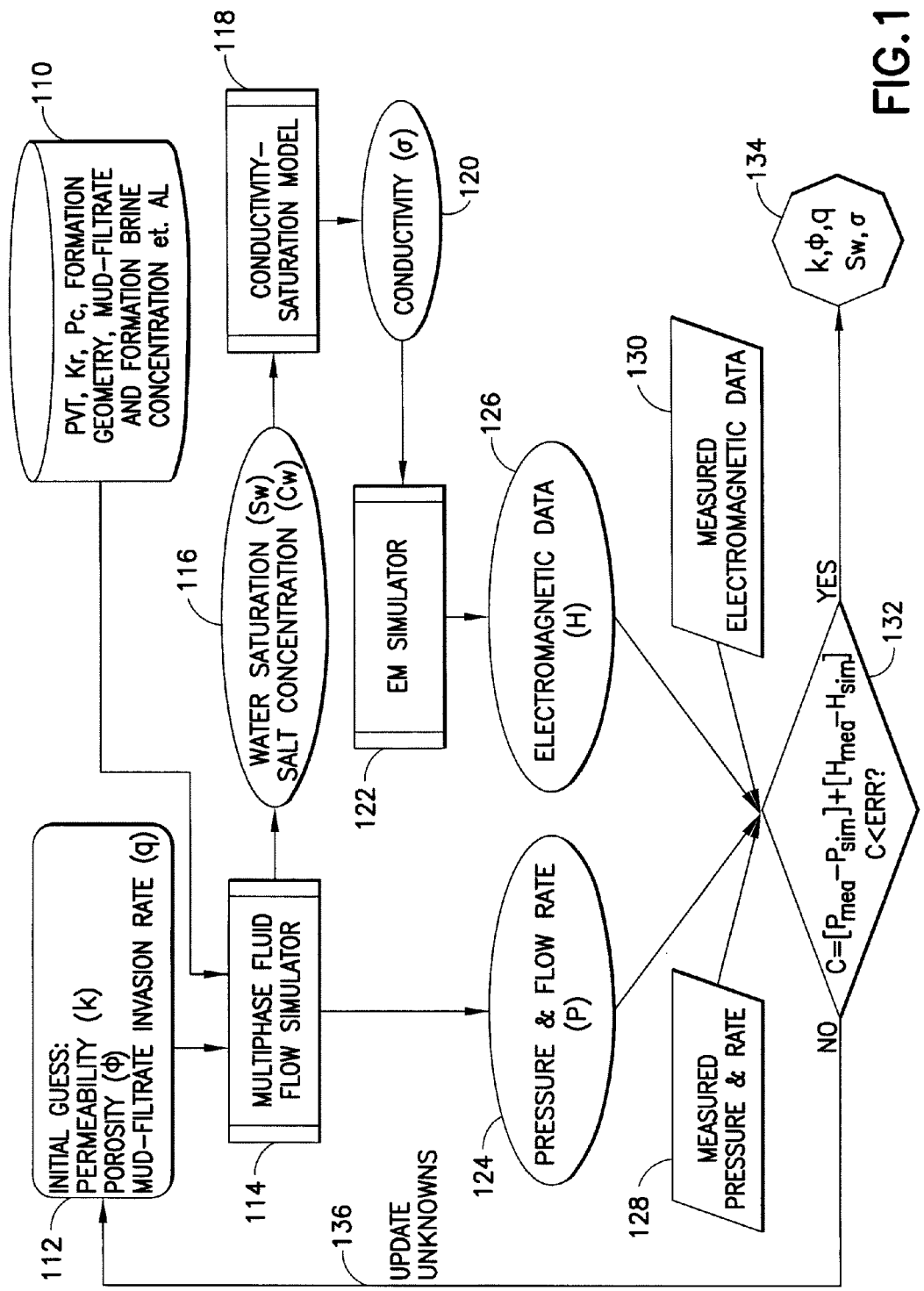
FIG. 1 is a flow chart showing workflow steps of a joint inversion, according to some embodiments.

It will be recognized by the person of ordinary skill in the art, given the benefit of this disclosure, that certain dimensions, features, components, and the like in the figures may have been enlarged, distorted or otherwise shown in a non-proportional or non-conventional manner to facilitate a better understanding of the technology disclosed herein.

DETAILED DESCRIPTION OF EXEMPLARY EMBODIMENTS

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Fluid Flow Simulation.

Further detail relating to fluid flow simulation, according to some embodiments, will now be provided. After a well is drilled the mud-filtrate invades into the surrounding rock formation. A three-phase, four-component (oil, water, gas, salt) model is employed to describe the mud-filtrate invasion process. The mud-filtrate invasion is simulated as an injection process by solving the pressure diffusive equation derived from Darcy's Law and the mass balance equation. Ignoring the chemical reactions and diffusive/dispersive transport, the mass balance equation for the fluid phase can be stated as follows (see Aziz and Settari (1979)):

$$\frac{\partial(\rho_l \phi S_l)}{\partial t} + \nabla \cdot (\rho_l v_l) = -q_l, \quad l = 1, 2, 3, \tag{1}$$

where the subscript l is the index of phase, which can be oil, water or gas. The symbols $\rho$, $\sigma$, $\phi$, q and S denote the fluid density, fluid velocity, porosity, source term, and phase saturation, respectively. The symbol $\nabla$ denotes the spatial differentiation with respect to spatial position (x, y, z). Darcy's law is used as the constitutive equation for the velocity vector, i.e., $$v_l = -k \cdot \frac{k_{r,l}}{\mu_l} (\nabla p_l - \gamma_l \nabla D_z), \tag{2}$$

where k is the tensor absolute permeability, $k_r$ is the phase relative permeability, $\mu$ is the phase viscosity, p is the phase pressure, $\gamma$ is the phase specific gravity and $D_z$ is the vertical depth below a reference level. We assume that the fluid (oil and water) and rock compressibilities are defined by:

$$c_{fluid} = -\frac{1}{V} \frac{\partial V}{\partial p}\bigg|_T = \frac{1}{\rho} \frac{\partial \rho}{\partial p}\bigg|_T, \tag{3}$$

and $$c_{rock} = \frac{1}{\phi} \frac{\partial \phi}{\partial p}\bigg|_T. \tag{4}$$

They are constant over the pressure range of interest in the simulation. The gas compressibility is treated as a function of the pressure-volume-temperature (PVT) properties of gas for each time-step. Additional relations about capillary pressures and fluid saturations are given by:

$$p_c = p_{nw} - p_w, \tag{5}$$

and $$\sum_l S_l = 1 \tag{6}$$

where the subscripts nw and w stand for the nonwetting and the wetting phase.

Salt is the forth component which is simulated, according to some embodiments. Assuming there is a high salt concentration contrast between the injected fluid and the in-situ formation brine and ignoring the diffusive/dispersive transport, the isothermal salt mixing in the aqueous-phase is solved by using the convective transport equation as follows:

$$\frac{\partial(\rho_w \phi S_w C_w)}{\partial t} + \nabla \cdot (\rho_w v_w C_w) = -C_{wi} q_i, \tag{7}$$

where $C_w$, $C_{wi}$ and $q_i$ is the salt concentration of formation brine, the salt concentration of invading fluid and the fluid injection rate, respectively. In our study the above equations are solved numerically using a finite-difference based reservoir simulator in fully implicit, black-oil mode with brine tracking option (e.g. ECLIPSE™). The pressure transient in the well/formation test can be simulated as well as the temporal and spatial distribution of the phase saturation and the salt concentration. In this description, focus is made on the scenario where a single well penetrates layered hydrocarbon-bearing formations. In the case of a vertical well, a cylindrical axisymmetric model is used in the numerical simulation and a logarithmic radial grid with very fine cells around the borehole is used to honor the mud-filtrate invasion and accurately catch the pressure transient phenomena in the well/formation test.

Electromagnetic Simulation.

Further detail relating to electromagnetic simulation, according to some embodiments, will now be provided. Electromagnetic responses measured by the array induction tools can be numerically simulated by solving a frequency-domain electromagnetic induction problem, which is described by the following diffusive Maxwell's equations:

$$\nabla \times E + i\omega \mu H = 0, \tag{8}$$

$$\nabla \times H - \sigma E = -J, \tag{9}$$

where E is the electric field vector, H is the magnetic field vector and J is the external electric current source vector. The symbols $\sigma = \sigma(x, y, z)$ and $\mu$ denote the electrical conductivity and the magnetic permeability (which is constant). The symbol $\omega$ denotes the radial frequency and $i = \sqrt{-1}$. By substituting equation (8) into equation (9) we obtain:

$$\sigma^{-1} \nabla \times \nabla \times E + i\omega E = -i\omega \sigma^{-1} J \tag{10}$$

A frequency-domain finite-difference algorithm such as described in Druskin, V., L. Knizhnerman, and P. Lee, 1999, New spectral lanczos decomposition method for induction modeling in arbitrary 3d geometry: Geophysics, 64, 701-706 (herein after "Druskin et al. (1999)"), incorporated herein by reference, is employed to numerically solve equation (10) on a staggered Yee grid (See, Yee, K. S., 1966, Numerical solution of initial boundary value problems involving maxwell's equations in isotropic media: IEEE Transactions on Antennas and Propagation, AP-14, 302-307). This approach uses a spectral Lanczos decomposition method (SLDM) with Krylov subspaces generated from the inverse powers of the Maxwell operator. Compared to the standard SLDM method, this so-called SLDMINV method is significantly more efficient. As shown in Druskin et al. (1999), the convergence rate of the SLDMINV method increases as the frequency decreases, this makes SLDMINV particularly attractive for low-frequency electromagnetic simulations.

Petrophysical Transform.

Further detail relating to petrophysical transforms, according to some embodiments, will now be provided. According to some embodiments, the spatial distribution of water saturation and salt concentration at logging times are computed by a multiphase fluid flow simulator such as ECLIPSE™ from Schlumberger. These are then transformed to a conductivity map using Archie's law (see, Archie, G. E., 1942, The electrical resistivity log as an aid in determining some reservoir characteristics: Petroleum Transactions of the AIME, 146, 54-62):

$$\sigma = \frac{\sigma_w \phi^m S_w^n}{a}, \quad (11)$$

where $\sigma_w$ is the brine conductivity and $S_w$ is the water saturation. Archie's parameters m, n and a are obtained from core measurements. The brine conductivity is a function of the salt concentration and temperature and is given by the following equation (see, Zhang, J.-H., Q. Hu, and Z.-H. Liu, 1999, Estimation of true formation resistivity and water saturation with a time-lapse induction logging method: The Log Analyst, 40, 138-148):

$$\sigma_w = \left[\left(0.0123 + \frac{3647.5}{C_w^{0.955}}\right)\frac{82}{1.8T+39}\right]^{-1}, \quad (12)$$

where $C_w$ is the salt concentration (ppm) and T is the formation temperature (° C.). In this example, The multiphase fluid flow model is solved on a cylindrical grid while solving the electromagnetic model on a Cartesian grid. A robust homogenization approach described in Moskow, S., V. Druskin, T. M. Habashy, P. Lee, and S. Davydycheva, 1999, A finite difference scheme for elliptic equations with rough coefficients using a cartesian grid nonconforming to interfaces: SIAM Journal on Numerical Analysis, 36, 442-464, incorporated herein by reference, is employed to map the conductivities from the three-dimensional (3D) cylindrical grid to the 3D Cartesian grid. This feature gives us more flexibility on constructing the model.

Inversion Algorithm.

Further detail relating to inversion algorithms, according to some embodiments, will now be provided. In the inversion process the electromagnetic data and pressure data (whenever available) are simultaneously inverted. After spatial discretization, the nonlinear inverse problem can be described by the following operator notations:

$$\overline{M}^e = \overline{S}^e(\overline{m}) + \overline{\epsilon}^e, \quad (13)$$

$$\overline{M}^p = \overline{S}^p(\overline{m}) + \overline{\epsilon}^p, \quad (14)$$

where $\overline{M}^e$ is the measured electromagnetic data while $\overline{M}^p$ is the measured pressure data. The components of these vectors are given by $$\overline{M}^e = [M(\overline{r}_i^s, \overline{r}_j^r, t_l), i=1, \ldots, N^s; j=1, \ldots, N^r; l=1, \ldots, N^l]^T, \quad (15)$$

$$\overline{M}^p = [M(\overline{r}_i^g, t_j), i=1, \ldots, N^g; j=1, \ldots, N^t]^T, \quad (16)$$

where $N^s$, $N^r$ and $N^l$ are the number of sources, receivers and logging snapshots in the electromagnetic measurements while $N^g$ and $N^t$ are the number of pressure gauges and time steps in the pressure measurements. In equations (13) and (14), $\overline{S}^e$ and $\overline{S}^p$ are the vector of simulated electromagnetic and pressure data as functions of the vector model parameter $\overline{m}$. The parametric model according to this example is layer by layer horizontal permeabilities, vertical permeabilities, porosities and average mud-filtrate invasion rates denoted by $k_h$, $k_v$, $\phi$ and q. The vector of model parameters is defined as follows:

$$\overline{m} = [k_{h;1}, k_{h;2}, \ldots, k_{h;L}, k_{v;1}, k_{v;2}, \ldots, k_{v;L}, \phi_1, \phi_2, \ldots, \phi_L, q_1, q_2, \ldots, q_L]^T, \quad (17)$$

where L is the number of layers in our one-dimensional (1D) parametric model. In equations (13) and (14), $\overline{\epsilon}^e$ and $\overline{\epsilon}^p$ denote the measurement errors in the electromagnetic and pressure data.

The inverse problems are posed as a minimization problem of the following cost function:

$$C_n(\overline{m}) = \left\|\overline{W}_d^e \cdot [\overline{M}^e - \overline{S}^e(\overline{m})]\right\|^2 + \left\|\overline{W}_d^p \cdot [\overline{M}^p - \overline{S}^p(\overline{m})]\right\|^2 + \lambda_n \|\ln(\overline{m}) - \ln(\overline{m}_n)\|^2, \quad (18)$$

where $\lambda_m$ is the regularization parameter at iteration n. In the regularization term, the logarithmic functions are employed since the unknown model parameters have different dimensions and can have different orders of magnitude. The diagonal matrices $\overline{W}_d^e$ and $\overline{W}_d^p$ are the data weighting matrices. There are several options for choosing these data weighting matrices. One particular choice is to account for all data points on equal footing. Hence, the data weighting matrices can be defined as follows:

$$W_{d;i,i}^e = \frac{1}{\sqrt{N^e |M_i^e|}}, \; i = 1, \ldots, N^e, \quad (19)$$

$$W_{d;i,i}^p = \frac{1}{\sqrt{N^p |M_i^p|}} \; i = 1, \ldots, N^p \quad (20)$$

where $N^e = N^s \times N^r \times N^l$ and $N^p = N^g \times N^t$. Substituting equations (19) and (20) into equation (18) we arrive at $$C_n(\overline{m}) = \frac{1}{N^e} \sum_{i=1}^{N^e} \left|\frac{M_i^e - S_i^e(\overline{m})}{M_i^e}\right|^2 + \frac{1}{N^p} \sum_{i=1}^{N^p} \left|\frac{M_i^p - S_i^p(\overline{m})}{M_i^p}\right|^2 + \lambda_n \sum_{l=1}^{4L} |\ln(m_l) - \ln(m_{n,l})|^2, \quad (21)$$

Another choice is to apply uniform weighting on all data points as follows:

$$W_{d;i,i}^e = \frac{1}{\sqrt{\sum_{j=1}^{N^e} |M_j^e|^2}}; \; i = 1, \ldots, N^e, \quad (22)$$

$$W_{d;i,i}^{p} = \frac{1}{\sqrt{\sum_{j=1}^{NP}|M_{j}^{p}|^{2}}}, i = 1, \ldots, N^{p}, \quad (23)$$

Substituting equations (22) and (23) into equation (18) we arrive at $$C_n(\overline{m}) = \frac{\sum_{i=1}^{N^e}|M_i^e - S_i^e(\overline{m})|^2}{\sum_{i=1}^{N^e}|M_i^e|^2} + \frac{\sum_{i=1}^{NP}|M_i^p - S_i^p(\overline{m})|^2}{\sum_{i=1}^{NP}|M_i^p|^2} + \lambda_n \sum_{l=1}^{4L}|\ln(m_l) - \ln(m_{n,l})|^2. \quad (24)$$

The minimization process is done by using the Gauss-Newton approach described in Habashy and Abubakar, incorporated herein by reference. The gradient vector of the cost function in equation (18) is given by $$g_i(\overline{m}) = \nabla_{m_i} C_n(\overline{m}) \quad (25)$$
$$= \sum_{j=1}^{N^e} J_{j,i}^e(\overline{m}) W_{d;j,i}^e W_{d;j,j}^e [M_j^e - S_j^e(\overline{m})] +$$
$$\sum_{j=1}^{NP} J_{j,i}^p(\overline{m}) W_{d;j,i}^p W_{d;j,j}^p [M_j^p - S_j^p(\overline{m})] +$$
$$\lambda_n \frac{1}{m_i}[\ln(m_i) - \ln(m_{n,i})]^2,$$

$$i = 1, \ldots, 4L$$

Hence, the gradient vector at the n-th iteration is given by $$g_{n,i} = g_i(\overline{m}_n) = \sum_{j=1}^{N^e} J_{j,i}^e(\overline{m}_n) W_{d;j,j}^e W_{d;j,j}^e [M_j^e - S_j^e(\overline{m}_n)] + \quad (26)$$
$$\sum_{j=1}^{NP} J_{j,i}^p(\overline{m}_n) W_{d;j,j}^p W_{d;j,j}^p [M_j^p - S_j^p(\overline{m}_n)].$$

The jacobian matrices are calculated using finite-difference approximations as follows:

$$J_{j,i}^e(\overline{m}_n) = -\frac{\partial S_j^e(\overline{m})}{\partial m_i}\bigg|_{\overline{m}=\overline{m}_n} \quad (27)$$
$$\approx -\frac{S_j^e(\overline{m}_n + \delta_{i,k}\Delta\overline{m}_n) - S_j^e(\overline{m}_n)}{\Delta m_{n,i}},$$

$$j = 1, \ldots, N^e, i, k = 1, \ldots, 4L$$

and $$J_{j,i}^p(\overline{m}_n) = -\frac{\partial S_j^p(\overline{m})}{\partial m_i}\bigg|_{\overline{m}=\overline{m}_n} \quad (28)$$
$$\approx -\frac{S_j^p(\overline{m}_n + \delta_{i,k}\Delta\overline{m}_n) - S_j^p(\overline{m}_n)}{\Delta m_{n,i}},$$

$$j = 1, \ldots, N^p, i, k = 1, \ldots, 4L$$

The Hessian matrix is given by $$H_{i,k}(\overline{m}) = \nabla_{m_q}\nabla_{m_i} C_n(\overline{m}) \quad (29)$$
$$\approx \sum_{j=1}^{N^e} J_{j,i}^e(\overline{m}) W_{d;j,j}^e W_{d;j,j}^e J_{j,k}^e(\overline{m}) +$$
$$\sum_{j=1}^{NP} J_{j,i}^p(\overline{m}) W_{d;j,j}^p W_{d;j,j}^p J_{j,k}^p(\overline{m}) +$$
$$\lambda_n \frac{1}{m_i}\frac{1}{m_k},$$

$$i, k = 1, \ldots, 4L$$

Hence, the Hessian matrix at the n-th iteration is given by $$H_{i,k}(\overline{m}_n) \approx \sum_{j=1}^{N^e} J_{j,i}^e(\overline{m}_n) W_{d;j,j}^e W_{d;j,j}^e J_{j,k}^e(\overline{m}_n) + \quad (30)$$
$$\sum_{j=1}^{NP} J_{j,i}^p(\overline{m}_n) W_{d;j,j}^p W_{d;j,j}^p J_{j,k}^p(\overline{m}_n) + \lambda_n \frac{1}{m_{n,i}}\frac{1}{m_{n,k}}.$$

In the Gauss-Newton minimization process, the search vector $p_n$ can be constructed from the following linear equation:

$$\overline{\overline{H}}_n \overline{p}_n = -\overline{g}_n. \quad (31)$$

Equation (31) is solved via a Gauss elimination procedure. The regularization parameter $\lambda_m$ is chosen as follows:

$$\lambda_n = \beta\max\{\tau_i\}, \text{ if } \frac{\min\{\tau_i\}}{\max\{\tau_i\}} < \beta, i = 1, \ldots, 4L, \quad (32)$$

where $\beta$ is a constant value determined from numerical experiments and $\tau$ are the eigenvalues of the Hessian matrix $\overline{\overline{H}}$.

We employ a line-search procedure as in Habashy and Abubakar to enforce the reduction of cost function in each iteration as follows:

$$\overline{m}_{n+1} = \overline{m}_n + v\overline{p}_n, \quad (33)$$

where $0 < v_n \leq 1$ is the step-length. The step-length is calculated by solving the minimization problem:

$$v_n = \underset{v}{\operatorname{argmin}}\{C(\overline{m}_n + v\overline{p}_n)\}. \quad (34)$$

In order to avoid expensive evaluation of the cost function $C(\overline{m})$, we adopt an algorithm (see Dennis Jr., J. E. and R. B. Schnabel, 1983, Numerical methods for unconstrained optimization and nonlinear equations: Prentice Hall, Inc., New Jersey) whereby $v_n$ is selected such that the average rate of decrease from $C(\bar{m}_n)$ to $C(\bar{m}_n+v_n\bar{p}_n)$ is at least some prescribed fraction, $\alpha$, of the initial rate of decrease at $\bar{m}_n$ along the direction $\bar{p}_n$, i.e., $$C(\bar{m}_n+v_n\bar{p}_n) \le C(\bar{m}_n)+\alpha v_n \delta C_{n+1}, \quad (35)$$

where $0<\alpha<1$ is a fractional number which, in practice, is set quite small (we use $10^{-4}$ herein) so that hardly more than a decrease in function value is required. $\delta C_{n+1}$ is the rate of decrease of $C(\bar{m})$ at $\bar{m}_n$ along the direction $\bar{p}_n$ and is given by:

$$\delta C_{n+1} = \frac{\partial}{\partial v} C(\bar{m}_n + v\bar{p}_n)\bigg|_{v=0} = \bar{g}^T(\bar{m}_n)\cdot\bar{p}_n. \quad (36)$$

We first employ the full Gauss-Newton search step in the minimization process. If $v_n=1$ fails to satisfy the criterion given by equation (35), then we reduce $v_n$ to backtrack along the direction $\bar{p}_n$ until an acceptable next $\bar{m}_{n+1}$ is found. Assume, at the (n+1)-th Gauss-Newton iteration, $v_n^k$ is the current step-length that does not satisfy equation (35), we compute the next backtracking step-length, $v_n^{k+1}$, by searching for the minimum of the cost function, $f(v) \equiv C(\bar{m}_n+v\bar{p}_n)$, which can be approximated by a quadratic expression. Thus, $v_n^{k+1}$, which is the minimum of $f(v)$, for $k=0, 1, 2, \ldots$ is given by:

$$v_n^{k+1} = -\frac{(v_n^k)^2}{2} \frac{\delta C_{n+1}}{C(\bar{m}_n+v_n^k\bar{p}_n)-C(\bar{m}_n)-v_n^k\delta C_{n+1}}. \quad (37)$$

To impose a priori information of maximum and minimum bounds on the unknown parameters, we constrained them using a non-linear transformation of the form:

$$m = f(c, m_{min}, m_{max}) = m_{min} + \frac{m_{max}-m_{min}}{c^2+1}c^2, \quad (38)$$

$$-\infty < c < +\infty.$$

The Gauss-Newton search step in m, $p_n = m_{n+1}-m_n$, is related to the step in c, $q_n = c_{n+1}-c_n$, by $$p = \frac{dm}{dc}q = 2\frac{m_{max}-m}{m_{max}-m_{min}}\sqrt{(m_{max}-m)(m-m_{min})}\,q. \quad (39)$$

The inverted parameter m is then updated using the following equation, $$m_{n+1} = m_{min} + \frac{m_{max}-m_{min}}{\alpha_n^2+(m_n-m_{min})(m_{max}-m_n)^3}\alpha_n^2, \quad (40)$$

where $$\alpha_n = (m_n-m_{min})(m_{max}-m_n) + \frac{1}{2}(m_{max}-m_{min})v_n p_n. \quad (41)$$

FIG. 1 is a flow chart showing workflow steps of a joint inversion, according to some embodiments. The initial guess of the unknown parameters (permeability, porosity and mud-filtrate invasion rate) 112 and additional information such as PVT, Kr, Pc, formation geometry, mud-filtrate and formation brine concentration et al. 110 are used for building a reservoir model. A multiphase fluid flow simulator 114 is run on the reservoir model generated from the data 110 and the initial parameters 112, thereby generating spatial distributions 116 of water saturation and salt concentration. A conductivity-saturation model 118 is used to transform the spatial distributions 116 into a conductivity distribution 120. Electromagnetic simulator 122 generates simulated electromagnetic data 126 based on the input conductivity distribution 120. Simulated pressure and flow rate data 124 is generated by multiphase fluid flow simulator 114. The pressure and flow rate data 124, electromagnetic data 126, measured pressure and flow rate data 128, and measured electromagnetic data 130 are input into cost function 132. Cost function 132 is combination of differences of 124 to 128, and 126 to 130. In step 136, values are updated for permeability, porosity and mud-filtrate invasion rate 112 until the cost function 132 becomes less than a predefined tolerance, thereby yielding the inverted parameters and derived distributions of water saturation and conductivity 134.

Test Cases.

Further detail relating to two test cases, according to some embodiments, will now be provided. To demonstrate the workflow, according to some embodiments, two synthetic examples were employed consisting of a vertical well penetrating layered hydrocarbon-bearing horizontal formations with sealing upper and lower shoulder beds. For reasons of facilitating comparisons with known results, the same examples are employed which can be referred to in Alpak, et al. (2004).

In this example, it is assumed that there is no-flux surrounding the boundaries. The water-based mud-filtration invasion is taking place since the well is drilled. The induction logging data are assumed to be recorded using an array induction tool, which has one transmitter and an eight-receiver array, providing fourteen pairs of apparent conductivity logs for different depths of investigation. Immediately after the first induction logging, a formation test is carried out using a packer-probe formation tester such as with Schlumberger's Modular Formation Dynamics Tester (MDT) tools. Three time-series of pressure transient measurements are recorded at two probes and the packer interval. This is followed by a second induction logging to sense the perturbed resistivity around the packer interval caused by the formation test. This process is referred to as a log-test-log mode. If the perturbation caused by the formation test is not significant, the second induction logging can be discarded, so the process is simplified to the log-test mode. In these two modes there are two measurements, namely the induction logging and pressure transient data, which are then used for the joint inversion. According to some embodiments, another mode is provided that only uses two induction logging data collected at different times. This mode is referred to herein as a time-lapse log mode. In a time-lapse log mode, the multiphase fluid flow simulator is only used to constrain the inversion of the induction logging data.

Figure 2A:
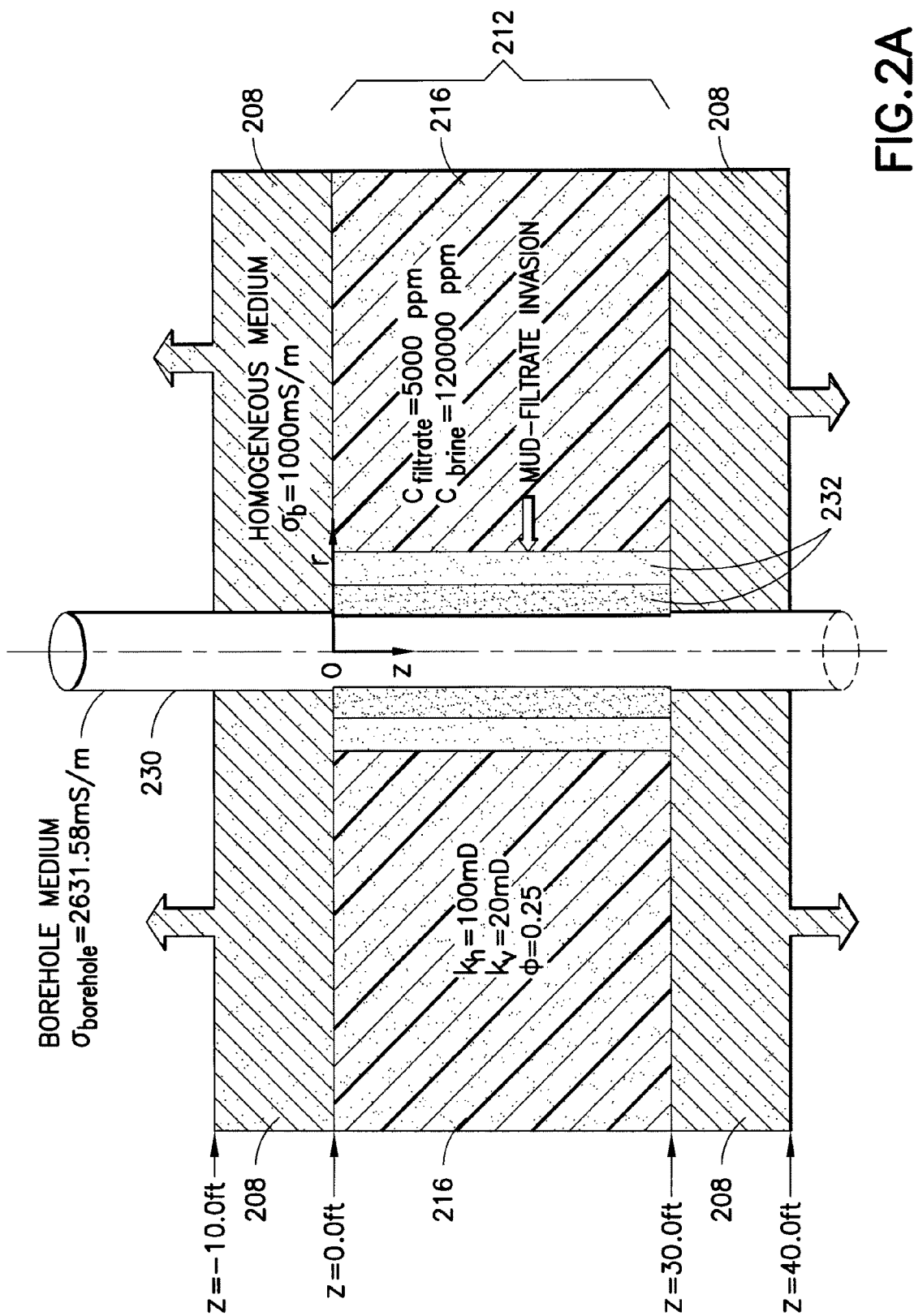
FIGS. 2A and 2B are diagrams showing certain configurations, according to some embodiments.
Figure 2B:
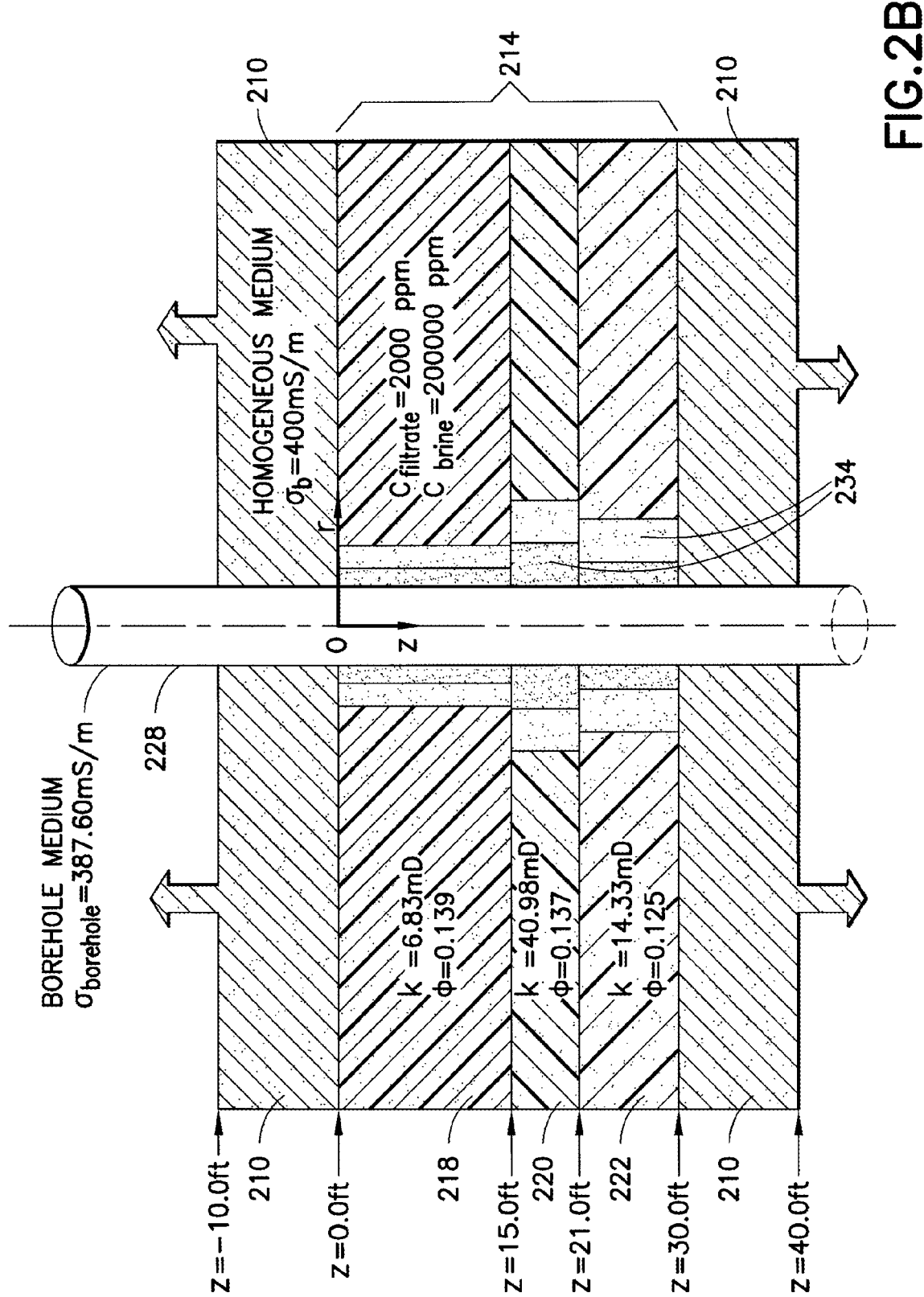

FIGS. 2A and 2B are diagrams showing certain configurations (refer to Alpak, et al. (2004)), according to some embodiments. For FIGS. 2A and 2B the drainage radii for wells 230 and 228 respectively, are both about 300 m. FIGS. 2A and 2B are two-dimensional vertical cross-sections of the reservoir model configuration. Impermeable shoulder beds 208 and 210 with known homogeneous formation conductivities are superimposed on the top and bottom of the reservoirs 212 and 214 respectively. The permeable zones of interest are subject to the water-based mud-filtrate invasion. In FIG. 2A, the reservoir 212 comprises a single-layer TI-anisotropic formation 216 with oil-water system. Mud filtrate invasion zones 232 for well 230, and 234 for well 228 are shown in FIGS. 2A and 2B respectively.

The case shown in FIG. 2A is a single-layer model with a TI-anisotropic formation and oil-water system, while the case shown in FIG. 2B is a three-layer model with isotropic formation and gas-water system. In these examples, the fluid properties, saturation dependent functions and the parameters in Archie's equation are available from laboratory and core measurements. Both the oleic and aqueous phases are slightly compressible while the gaseous phase is compressible with its compressibility dependent on pressure.

Figure 3A:
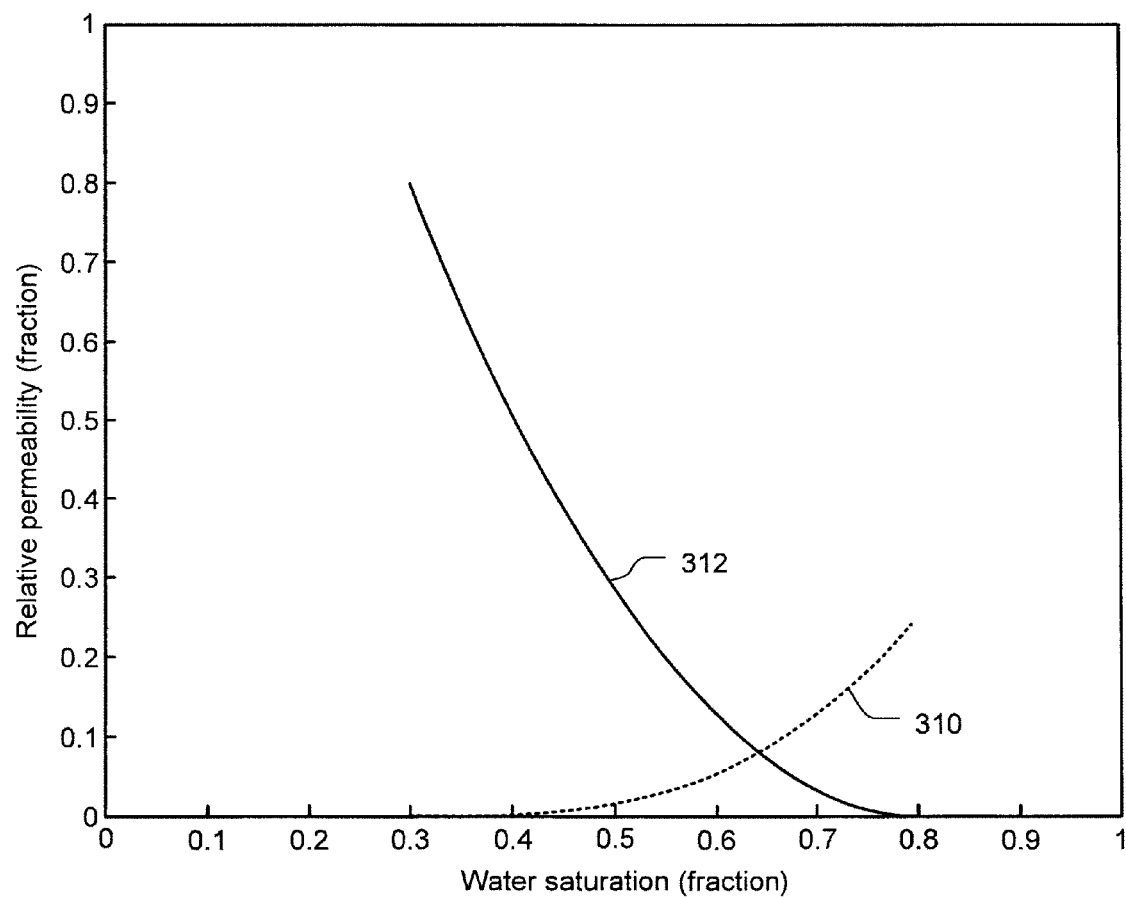
FIGS. 3A, 3B and 3C are plots illustrating the saturation dependent functions used in certain described examples.
Figure 3B:
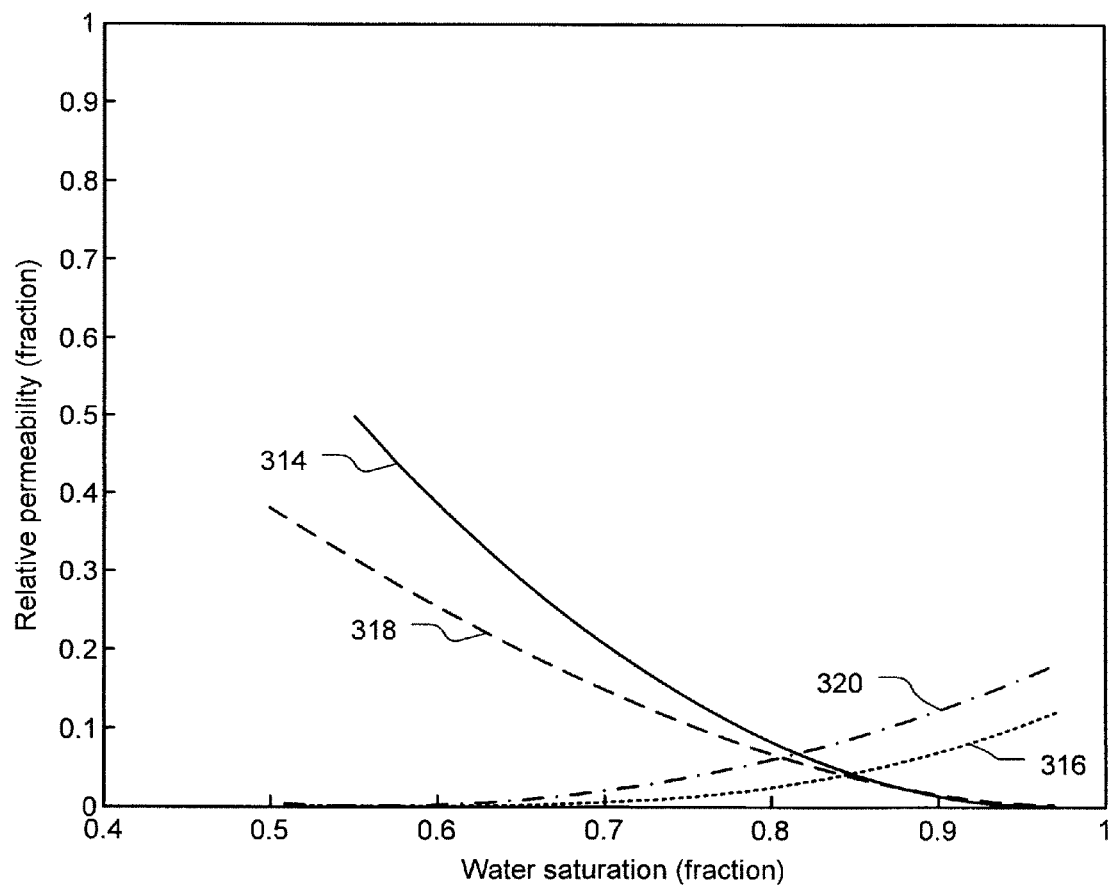
Figure 3C:
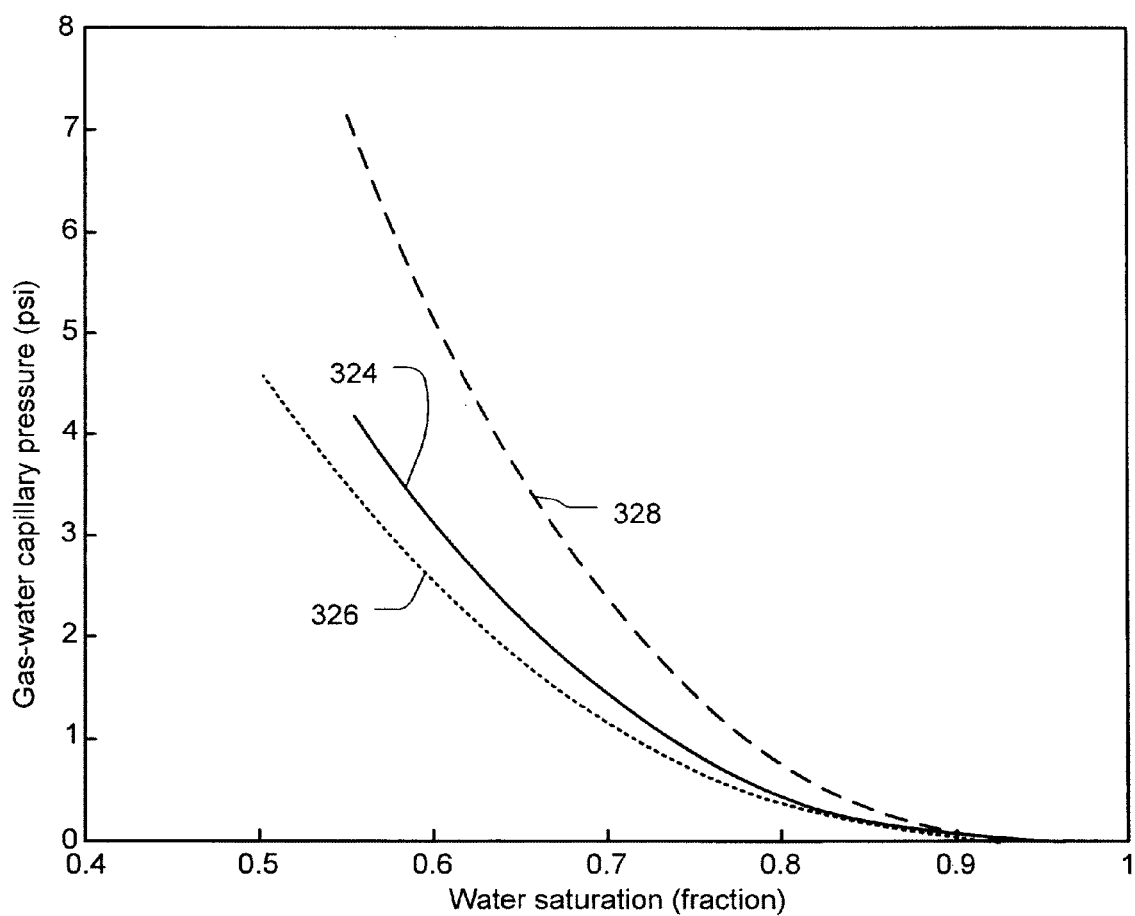

FIGS. 3A, 3B and 3C are plots illustrating the saturation dependent functions used in certain described examples (refer to Alpak, et al. (2004)). FIG. 3A shows the relative permeability for the oil-water case shown in FIG. 2A, where the capillary pressure is negligible. Curve 310 is the relative permeability of water and curve 312 is the relative permeability of oil in the formation layer 214. FIG. 3B shows the layer-by-layer relative permeability for the gas-water case shown in FIG. 2B. Curve 314 shows the relative permeability for gas in the upper and lower layers 218 and 222; curve 316 shows the relative permeability for water in the upper and lower layers 218 and 222; curve 318 shows the relative permeability of gas for the middle layer 220; and curve 320 shows the relative permeability of water for the middle layer 220. FIG. 3C shows the layer-by-layer capillary pressure for gas-water case shown in FIG. 2C. Curve 324 shows the capillary pressure for the upper layer 118; curve 326 shows the capillary pressure for the middle layer 220; and curve 328 shows the capillary pressure for the lower layer 222.

For the oil-water case shown in FIG. 2A, the following operation schedule is assumed: The well is subjected to the mud-filtrate invasion after drilling. The first induction log is recorded on the third day and then immediately followed by the wireline formation test, which is composed of a draw-down at a constant liquid rate of 4.76962 m$^3$/d for 100 minutes followed by a build-up for 200 minutes. In this example, the pressure transient data is only used in the build-up period for the inversion. Another induction log is then recorded to capture the perturbation caused by the formation test. For the time-lapse log mode, the second induction log is recorded at the tenth day.

In the fluid flow simulator we used a 31×6×30 grid with the finest radial cell size of about 0.0305 m, adjacent to the borehole. The model is initialized with the irreducible water saturation. Since the fluid and salt movement are convective and the diffusion and salt dispersion can be neglected, the mud-filtrate invasion process is calculated using an average mud-filtrate invasion rate. It is assumed that the average invasion rate is 0.0067 m$^3$/d/m for the first three days. For the time-lapse log mode, an invasion rate of 0.00577 m$^3$/d/m between the third and tenth day is also assumed. Other specific model parameters are listed in Table 1.

TABLE 1

Petrophysical and fluid parameters and other relevant information employed in oil-water example shows in FIG. 2A. (also, Refer to Alpak, et al. (2004))

| Variable | Value |
|---|---|
| Formation rock compressibility | 7.25'10$^{-8}$ [bar$^{-1}$] |
| Aqueous phase viscosity | 1.274 [cp] |
| Aqueous phase density | 1001.074 [kg/m$^3$] |
| Aqueous phase formation volume factor | 0.996 [rm$^3$/sm$^3$] |
| Aqueous phase compressibility | 3.7'10$^{-5}$ [bar$^{-1}$] |
| Oleic phase viscosity | 0.355 [cp] |
| Oleic phase API density | 42 [°API] |
| Oleic phase density | 815.564 [kg/m$^3$] |
| Oleic phase formation volume factor | 1.471 [rm$^3$/sm$^3$] |
| Oleic phase compressibility | 2.76'10$^{-4}$ [bar$^{-1}$] |
| Formation pressure (refer to formation top) | 206.84 [bar] |
| Wellbore radius | 0.108 [m] |
| Formation horizontal permeability | 100 [mD] |
| Formation vertical permeability | 20 [mD] |
| Formation porosity | 0.25 [fraction] |
| Formation temperature | 220 [° F.] |
| Formation brine salinity | 120000 [ppm] |
| Mud-filtrate salinity | 5000 [ppm] |
| a-constant in the Archie's equation | 1.00 [dimensionless] |
| m-cementation exponent in the Archie's equation | 2.00 [dimensionless] |
| n-water saturation exponent in the Archie's equation | 2.00 [dimensionless] |
| Mud conductivity | 2631.58 [mS/m] |
| Upper and lower shoulder bed conductivities | 1000.00 [mS/m] |
| Logging interval | 0.61 [m] |

In the gas-water three-layer example shown in FIG. 2B, a similar operation schedule is used. However, the first induction log is recorded at the first day, the draw-down for the formation test lasts 100 minutes at a constant rate of 0.2385 m$^3$/d, then the tool is shut down for another 200 minutes for pressure build-up. The second induction logging was not carried out since the perturbation in formation resistivity caused by the formation test is not significant. The fluid flow simulator uses a 91×6×30 grid with the finest radial cell size of about 0.0061 m. The model is initialized with the irreducible water saturation. Different average invasion rates, permeabilities and porosities are used for the three layers. Referring to FIG. 2B, for the first-layer 218: k=6.83 mD, ϕ=0.139, q=0.42523 m$^3$/d/m; for the second-layer 220: k=40.98 mD, ϕ=0.137, q=0.42485 m$^3$/d/m; and for the third-layer 222: k=14.33 mD, ϕ=0.125, q=0.42548 m$^3$/d/m. Other specific model parameters can be found in Table 2. Some parameters are the same as in oil-water example of FIG. 2A.

TABLE 2

Petrophysical and fluid parameters and other relevant information employed in example shown in FIG. 2B. (Also refer to Alpak, et al. (2004))

| Variable | Value |
|---|---|
| Aqueous phase viscosity | 1.000 [cp] |
| Aqueous phase density | 1186.007 [kg/m$^3$] |
| Aqueous phase formation volume factor | 1.000 [rm$^3$/sm$^3$] |
| Aqueous phase compressibility | 1.45'10$^{-5}$ [bar$^{-1}$] |
| Gaseous phase viscosity [f(p) for T = const.] | 0.01087 [cp] @ 1 bar |
| Gaseous phase density [f(p) for T = const.] | 0.977 [kg/m$^3$] @ 1 bar |
| Gaseous phase formation volume factor [f(p) for T = const.] | 0.782 [rm$^3$/sm$^3$] @ 1 bar |
| Formation pressure (refer to formation top) | 6.62 [bar] |
| Wellbore radius | 0.107 [m] |
| Formation temperature | 96 [° F.] |
| Formation brine salinity | 200000 [ppm] |
| Mud-filtrate salinity | 2000 [ppm] |
| Mud conductivity | 387.60 [mS/m] |
| Upper and lower shoulder bed conductivities | 400.00 [mS/m] |

Inversion Results.

Figure 4A:
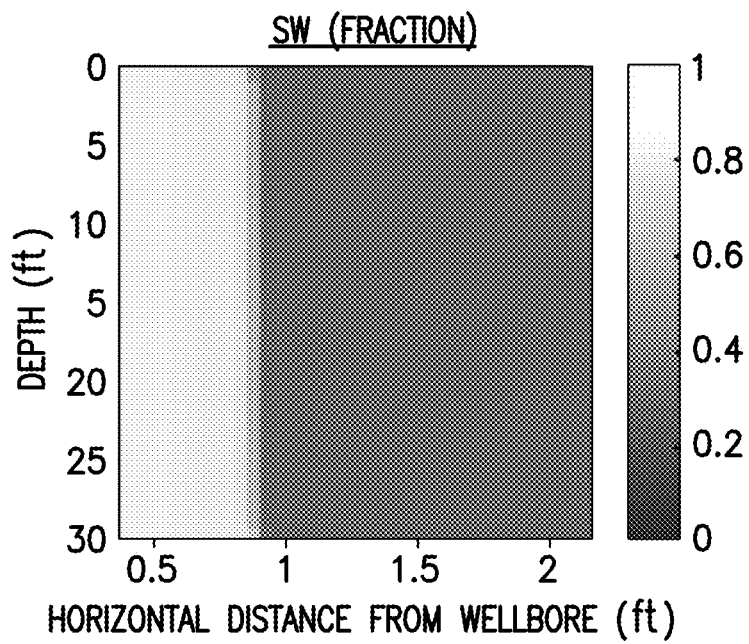
FIGS. 4A-4H, are vertical cross section diagrams show the results for oil-water example shown in FIG. 2A.
Figure 4B:
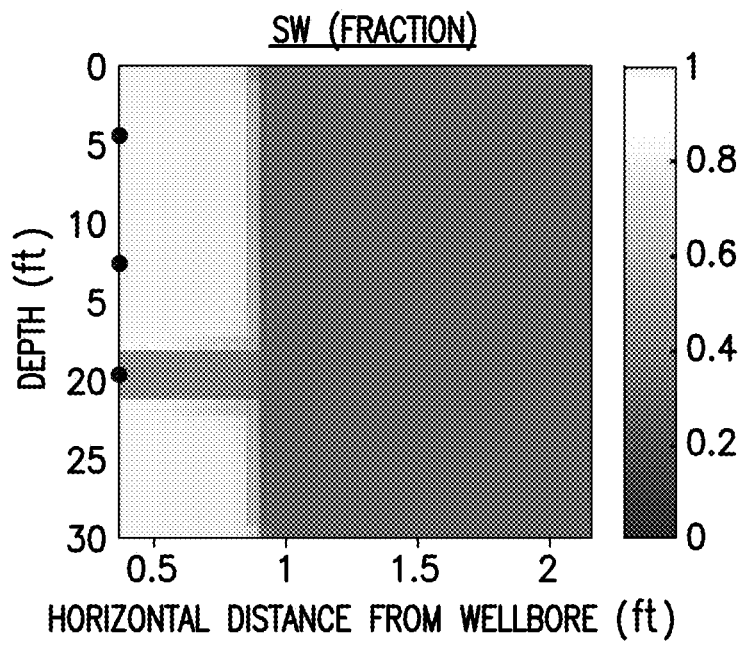
Figure 4C:
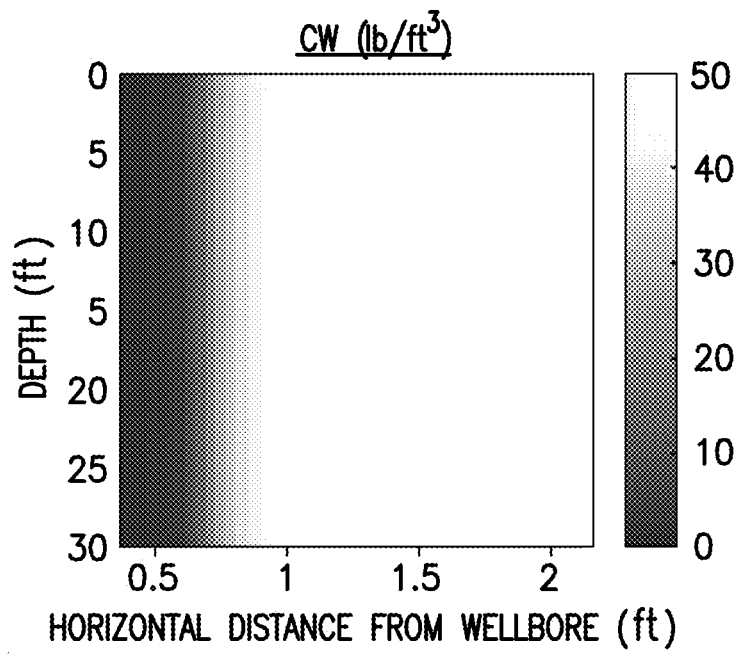
Figure 4D:
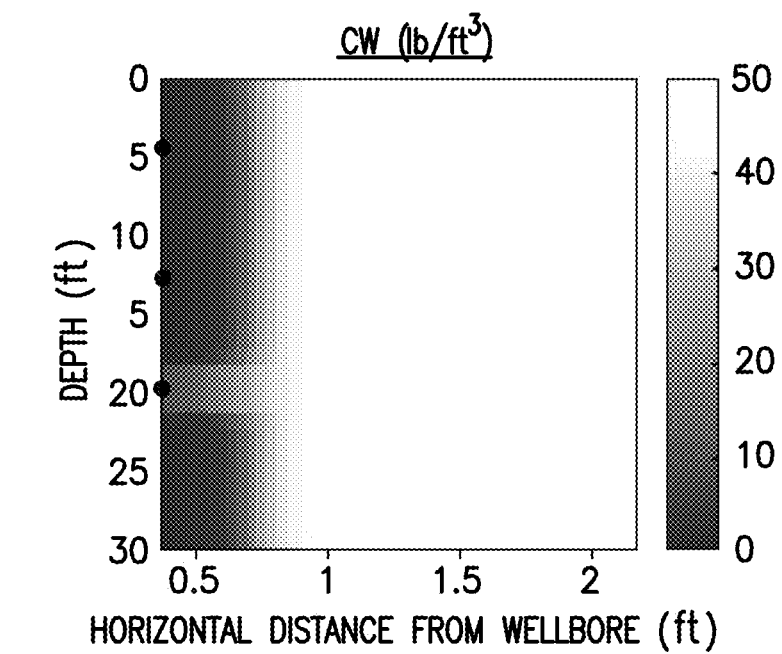
Figure 4E:
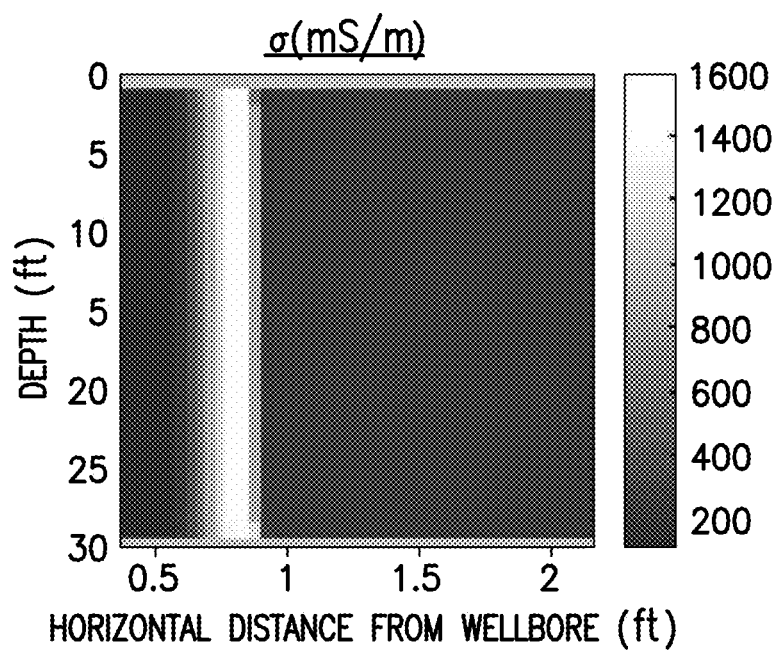
Figure 4F:
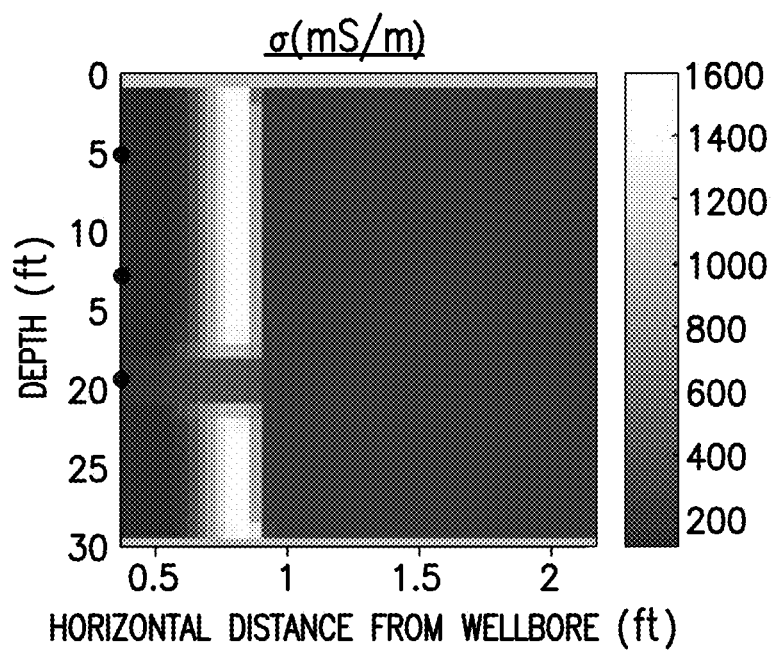
Figure 4G:
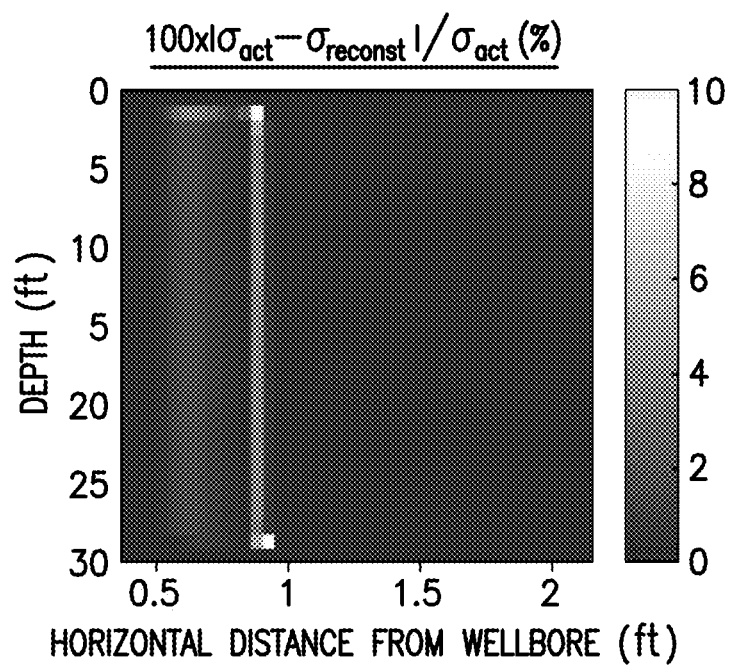
Figure 4H:
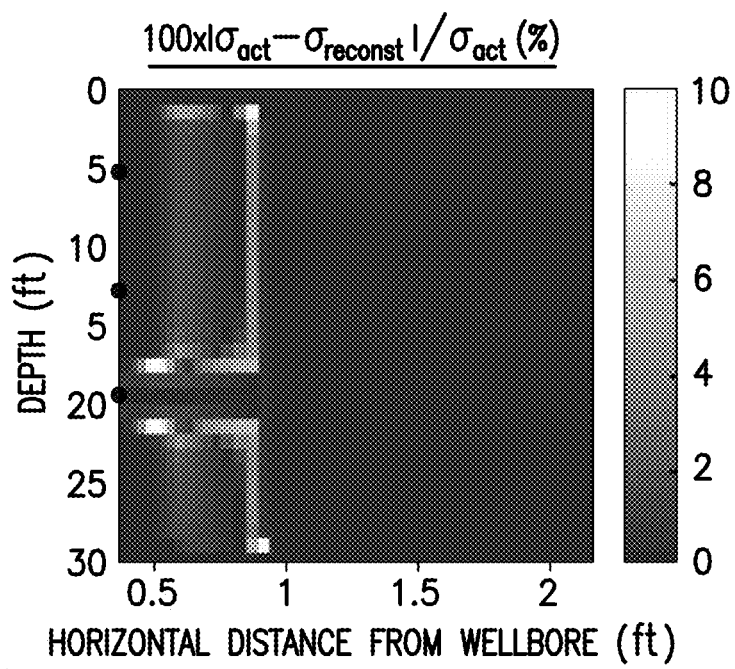

In this section, the inversion results are described for the synthetic induction logging data and pressure transient data, which are generated by forward modelling based on predefined true petrophysical parameters and invasion rates, with added zero-mean Gauss random noise. FIGS. 4-6, show the results for oil-water example shown in FIG. 2A. In FIG. 4A, diagram 410 shows the vertical cross-section of spatial distributions of the reconstructed water saturation for the first logging run for the oil-water example shown in FIG. 2A. In FIG. 4B, diagram 412 shows the vertical cross-section of spatial distributions of the reconstructed water saturation for the second logging run for the oil-water example shown in FIG. 2A. In FIG. 4C, diagram 414 shows the vertical cross-section of spatial distributions of the reconstructed salt concentration for the first logging run for the oil-water example shown in FIG. 2A. In FIG. 4D, diagram 416 shows the vertical cross-section of spatial distributions of the reconstructed salt concentration for the second logging run for the oil-water example shown in FIG. 2A. In FIG. 4E, diagram 418 shows the vertical cross-section of spatial distributions of the reconstructed formation conductivity for the first logging run for the oil-water example shown in FIG. 2A. In FIG. 4F, diagram 420 shows the vertical cross-section of spatial distributions of the reconstructed formation conductivity for the second logging run for the oil-water example shown in FIG. 2A. In all cases there was Gaussian random noise of up to 7%. A high conductivity annulus is observed, which is caused by the invasion of the low salinity water-based mud-filtrate into the hydrocarbon-bearing formation with high salinity connate water. FIGS. 4B, 4D and 4F show oil breaking through the high conductivity annulus caused by draw-down in the formation test. In FIG. 4G, diagram 422 plots the difference between the true conductivity and the reconstructed conductivity distributions for the first logging run for the oil-water example shown in FIG. 2A. In FIG. 4H, diagram 424 plots the difference between the true conductivity and the reconstructed conductivity distributions for the second logging run for the oil-water example shown in FIG. 2A. It can be seen from FIGS. 4H and 4G that there is good agreement between the true conductivity and reconstructed conductivity distributions.

Figure 5A:
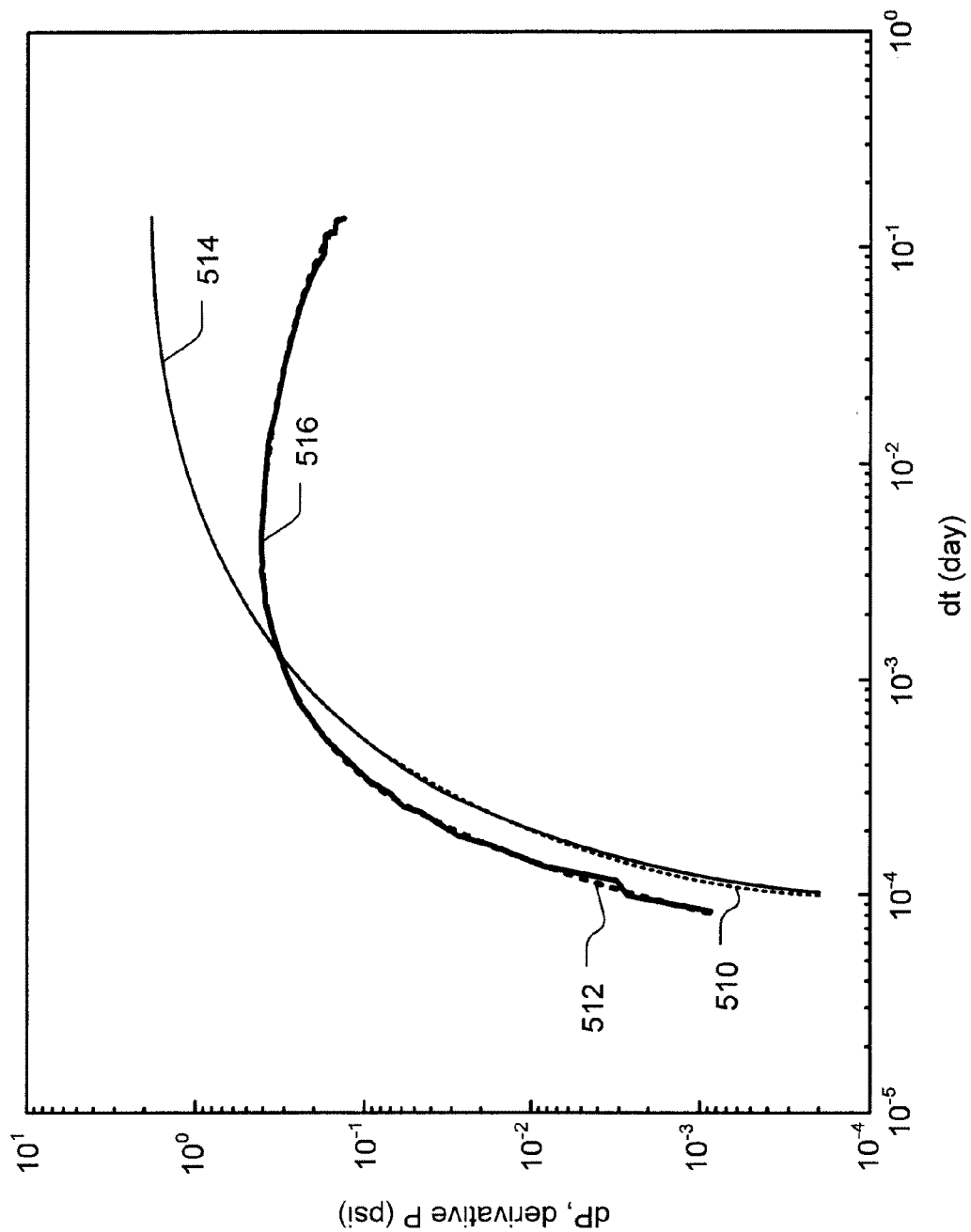
FIGS. 5A and 5B are log-log plots of the pressure and the pressure derivative for the build-up for the example shown in FIG. 2A.
Figure 5B:
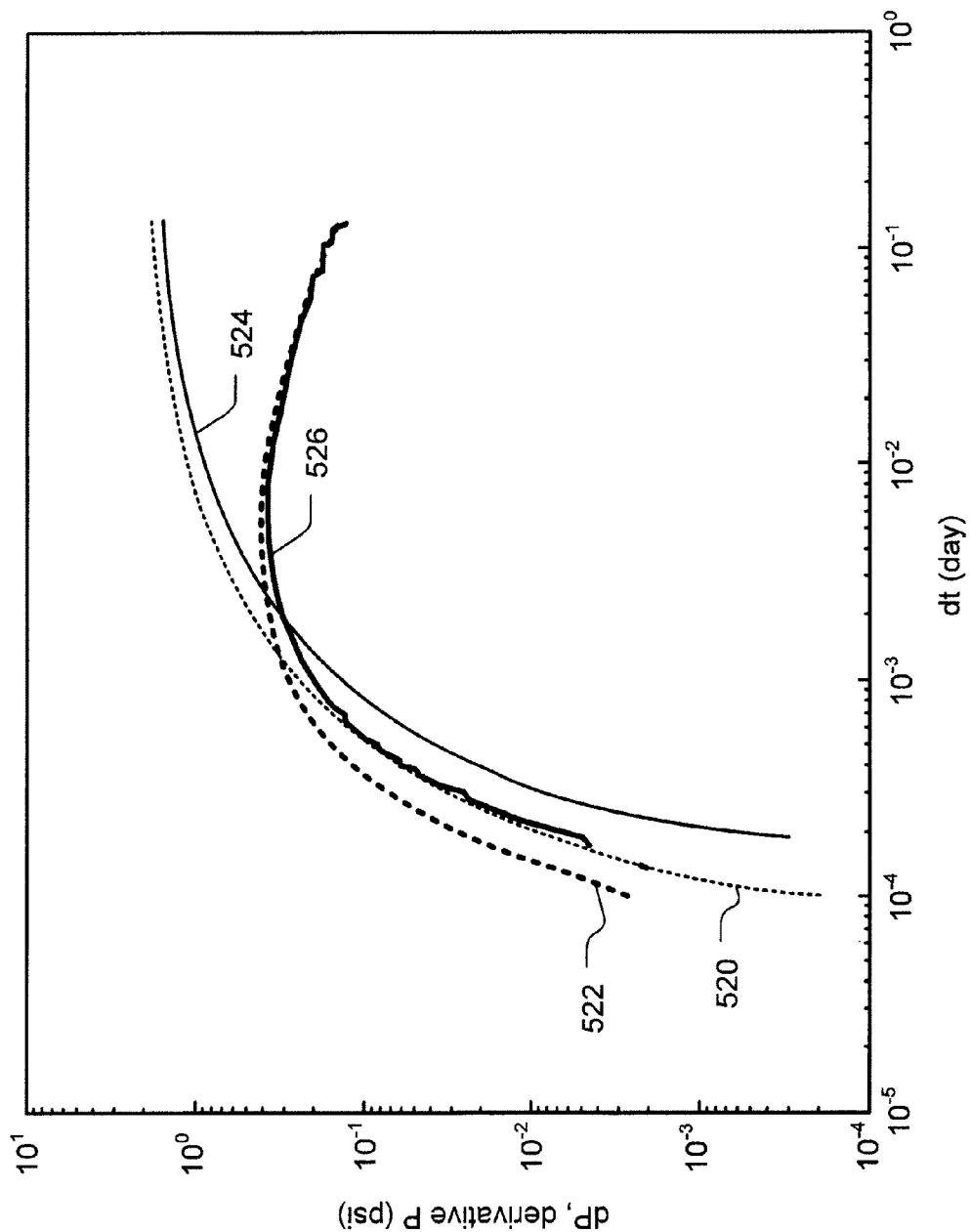
Figure 6:
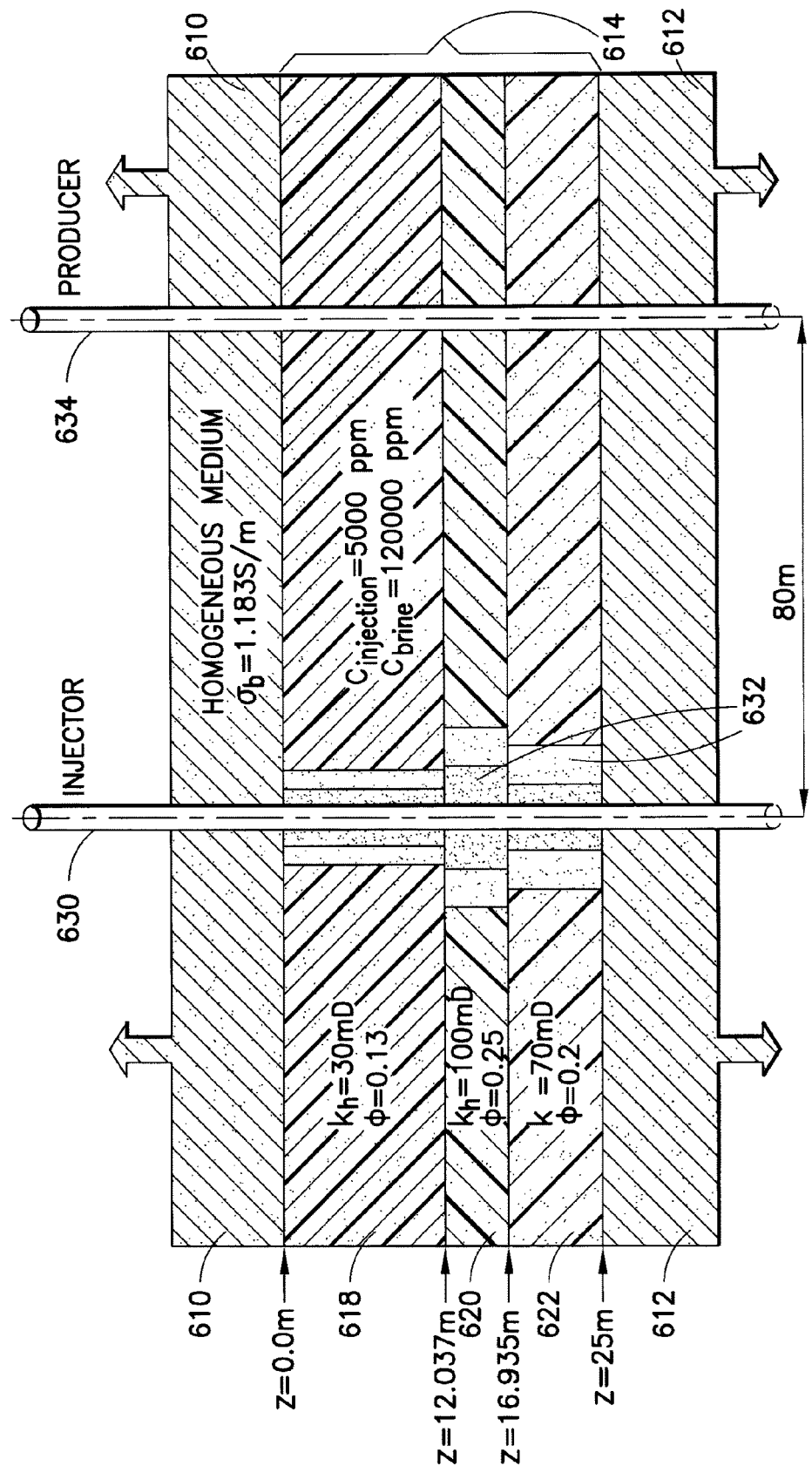
FIG. 6 is a two-dimensional vertical cross-section of a reservoir having an injector and producer well, according to some embodiments.

FIGS. 5A and 5B are log-log plots of the pressure and the pressure derivative for the build-up for the example shown in FIG. 2A. In FIG. 5A plots results with 0% noise, and in FIG. 5B plots results with 7% noise. In FIG. 5A, curve 510 plots the measured pressure, curve 512 plots the measured derivative pressure, curve 514 plots the post-inversion pressure, and curve 516 plots the post-inversion derivative pressure. In FIG. 5B, curve 520 plots the measured pressure, curve 522 plots the measured derivative pressure, curve 524 plots the post-inversion pressure, and curve 526 plots the post-inversion derivative pressure.

The inverted permeability, porosity and average mud-filtrate invasion rate are listed together with the number of Gauss-Newton iterations in Tables 3 and 4.

TABLE 3

Log-test-log inversion results for example shown in FIG. 2A
Log-test-log

|  | Add. Gauss noise level | $k_h$ (md) | $k_v$ (md) | $\phi$ (fraction) | q ($m^3$/d/m) | Num. of iterations |
|---|---|---|---|---|---|---|
| Init. guess |  | 40 | 40 | 0.12 | 0.00052 |  |
| True |  | 100 | 20 | 0.25 | 0.00670 |  |
| Inverted | 0% | 100.00 | 20.00 | 0.250 | 0.00670 | 8 |
| Inverted | 1% | 100.78 | 19.08 | 0.250 | 0.00670 | 6 |
| Inverted | 3% | 102.43 | 17.02 | 0.250 | 0.00670 | 5 |
| Inverted | 5% | 104.24 | 14.86 | 0.250 | 0.00672 | 7 |
| Inverted | 7% | 105.99 | 13.54 | 0.250 | 0.00672 | 6 |
| Analytic | 0% | 80.26 | 18.32 |  |  |  |

TABLE 4

Time-lapse log inversion results for example shown in FIG. 2A
Time-lapse log

|  | Add. Gauss noise level | k (md) | $\phi$ (fraction) | $q_1$ ($m^3$/d/m) | $q_2$ ($m^3$/d/m) | Num. of iterations |
|---|---|---|---|---|---|---|
| Init. guess |  | N/A | 0.12 | 0.001 | 0.00052 |  |
| True |  | N/A | 0.25 | 0.00670 | 0.00577 |  |
| Inverted | 0% | N/A | 0.250 | 0.00670 | 0.00577 | 4 |
| Inverted | 1% | N/A | 0.250 | 0.00677 | 0.00562 | 3 |
| Inverted | 3% | N/A | 0.249 | 0.00721 | 0.00526 | 2 |
| Inverted | 5% | N/A | 0.249 | 0.00732 | 0.00495 | 2 |

The inversion results demonstrate that we can obtain reliable horizontal permeability, porosity and average invasion rate for up to 7% noise level. The inversion of the porosity is very robust with little sensitivity to the noise level. This is because the induction logging data is governed by the formation conductivity, which is strongly affected by the porosity. With increasing noise level, the quality of the inverted vertical permeability quickly deteriorates. This is expected because the sensitivity of pressure transient measurements to the vertical permeability are relatively low and would be overwhelmed by noise. The inversion of the horizontal permeability shows good accuracy. In the time-lapse log mode, the formation permeability cannot be inverted from induction measurements only and without the pressure data since the invasion process is mainly governed by the mud-cake and moreover we are using average invasion rates as the boundary condition in the fluid flow simulation.

The horizontal and vertical permeabilities can also be independently obtained from the formation test by using the analytic straight-line computation, which is based on the single-phase model without taking into account the invasion profile. This approach can be applied on the pressure transient data, which are generated using the fluid flow simulator for the oil-water example shown in FIG. 2A. Only the build-up section of the data are interpreted. But the build-up time is prolonged to reach a stable radial flow status (FIGS. 5A and 5B show that the radial flow has not formed yet). No noise was introduced in this case to the synthetic pressure transient data. The analytical interpretation results of the build-up section are also listed in Table 3 for comparison. It can be observed that the joint inversion produces more accurate estimation of formation permeabilities.

TABLE 5

Log-test inversion results for example shown in FIG. 2B.

|  |  | Add. Gauss noise level | k (md) | $\phi$ (fraction) | q ($m^3$/d/m) | Num. of iterations |
|---|---|---|---|---|---|---|
|  | Init. guess |  | 12.39 | 0.18 | 0.26081 |  |
| Layer 1 | True |  | 6.83 | 0.139 | 0.42523 |  |
|  | Inverted | 0% | 6.83 | 0.139 | 0.42523 | 8 |
|  | Inverted | 5% | 6.61 | 0.139 | 0.41693 | 10 |
| Layer 2 | True |  | 40.98 | 0.137 | 0.42485 |  |
|  | Inverted | 0% | 40.98 | 0.137 | 0.42486 | 8 |
|  | Inverted | 5% | 47.15 | 0.139 | 0.47190 | 10 |
| Layer 3 | True |  | 14.33 | 0.125 | 0.42548 |  |
|  | Inverted | 0% | 14.33 | 0.125 | 0.42547 | 8 |
|  | Inverted | 5% | 14.33 | 0.123 | 0.40225 | 10 |

Thus, according to some embodiments, a parametric inversion algorithm is described to jointly invert the induction logging and pressure transient measurements, which can be used for the determination of the horizontal and vertical permeability, the porosity and the average mud-filtrate invasion rate for each flow unit or unit height. When using pressure measurements, this algorithm can reliably invert the permeability without incorporating a mud-cake growth and invasion model. Additionally, the porosity can be inverted robustly either using the induction log together with pressure measurement, or only by using induction logs but constrained by the fluid flow simulator.

Traditionally, the mud-filtrate invasion profile can be derived from the inversion of induction measurements, which are based on a simplified step-profile invasion model. Inversion of the induction logs constrained by the fluid flow simulator improves the estimation of the mud-filtrate invasion profile, which becomes consistent with the fluid flow physics. On the other hand, the conventional interpretation of formation test is based on the single-phase flow model without taking into account fluid invasion or the need to pump a long time to clean up the contamination of the mud-filtrate before the test procedure. The joint inversion of induction logging and pressure measurements enable a more reliable result. This technique can accommodate the existence of the mud-filtrate in the region of formation test, and hence can save costly rig time for clean up.

As a by-product, through the fluid-flow constrained time-lapse induction log inversion, the temporal and spatial distributions of the saturation and conductivity can be obtained, which can be used to monitor the fluid front movement. According to some embodiments, the inversion techniques described herein are used to generate a quantitative predictive formation model that is dynamic, rather than static, to perform fluid flow simulations.

According to some embodiments, the inversion procedures described herein with respect to mud-filtrate invasion rates are applied to estimate completion fluid invasion rates. For example the invasion zones 232 and 234 in FIGS. 2A and 2B respectively, according to these embodiments, represent completion fluid invasion zones. According to some embodiments, a subsequent electromagnetic survey can be conducted for the purpose of estimating the completion fluid invasion rates. However, according to other embodiments, a quantitative predictive formation model based on earlier electromagnetic surveys for mud filtrate invasion can also be used to directly predict the completion fluid invasion.

According to some embodiments, the result of the inversion procedures is used to aid well clean up job design. A "clean up" job can be performed following a drilling procedure and/or completion procedure to reduce the effects that the drilling fluid and/or completion fluid has on the producing formation. Based on the invasion profile and the quantitative predictive formation model derived from the inversion techniques described herein, a fluid flow simulation is performed to find out how the clean up procedure should be operated.

According to some embodiments, the described workflow can be applied to deviated and horizontal wells with dipping layers and cross-well applications. In these cases the cylindrical grid in the fluid flow simulator should be replaced by the Cartesian grid.

Figure 7:
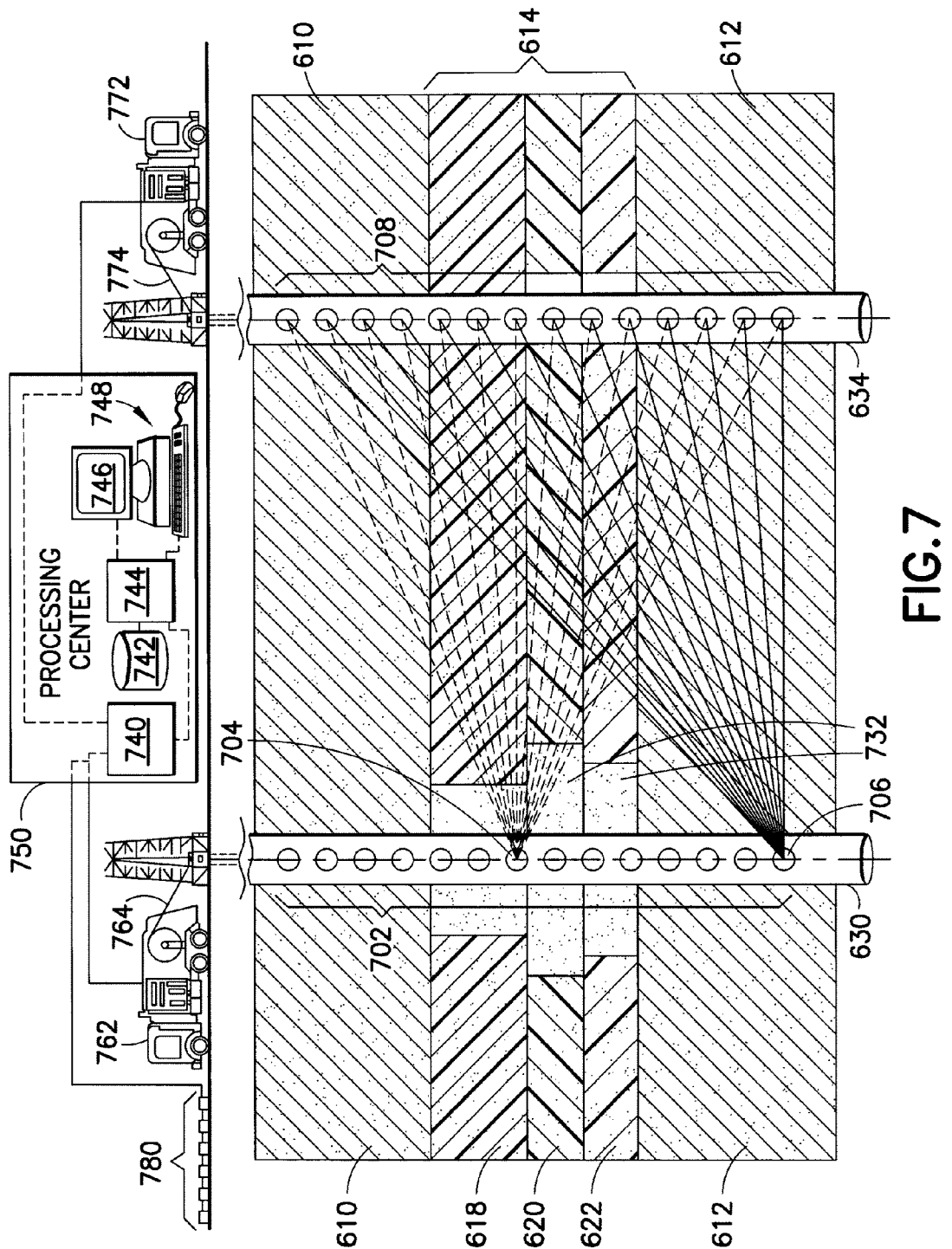
FIG. 7 shows the source-receiver setup and associated surface equipment according to the example shown in FIG. 6.

In addition to the 1D parametric inversions of porosity for each layer, according to some embodiments, the approach can also be applied to invert a spatial distribution of porosity. FIGS. 6 and 7 illustrate an example used to demonstrate this capability. FIG. 6 is a two-dimensional vertical cross-section of a reservoir having an injector and producer well, according to some embodiments. The reservoir 614 is composed of three layers, 618, 620 and 622, with a total thickness of 25 meters. The sealing upper and lower shoulder beds 610 and 612 allow for no-flux surrounding the boundaries. The permeability and porosity of each layer are different. The upper layer 618 has $k_h$=30 mD, the middle layer 620 has $k_h$=100 mD, and the lower layer 622 has $k_h$=70 mD. It is assumed that the formations are TI-anisotropic with constant anisotropy ratio, $k_v/k_h$=0.1. An injection well 630 and a production well 634 penetrate all the layers 610, 618, 620, 622 and 612. Both wells 630 and 634 are vertical and the separation is 80 meters. An oil-water system is used and it is assumed that the fluid properties, saturation dependent functions and coefficients used in the Archie's equation are available from laboratory and core measurements. For simplicity, it is assumed that the injection well 630 is operated under bottomhole pressure control, which is a constant 241.32 bar. The production well 634 produces a constant oil rate of 158.99 m³/d. After 5 days injection and production, a crosswell electromagnetic logging is conducted. Water flooding zone 632 is also shown.

FIG. 7 shows the source-receiver setup and associated surface equipment according to the example shown in FIG. 6. In the crosswell electromagnetic logging process, sources 702 are located in the injection well 630, while receivers 708 are located in the production well 634. Although only 14 source stations and 14 receiver stations are shown on the toolstrings in FIG. 7 for simplicity, in this example there are 29 source stations 702 and 29 receiver stations 708. Thus there are 29×29 source-receiver combinations. For example, each of the receivers 708 receiver signals form source 704 and from source 706 as shown by the dashed and solid lines in FIG. 7. The data are the vertical component of the magnetic fields and the sources operate at 500 Hz. For the fluid flow modelling, a 198×11×31 grid is used according to some embodiments. The grid is uniform and fine at the center region then logarithmically coarsened towards the boundaries in the x and y directions, however the grid is completely uniform in the z direction. The model is initialized with the irreducible water saturation. For the electromagnetic modelling, an 84×84 grid is used where the inner inversion domain is uniform and the outer domain is optimized automatically. It is assumed that the conductivities of shoulder beds are 1.183 S/m. According to some embodiments, the electromagnetic measurements are acquired using a tool or tools such as Schlumberger's Array Induction Imager Tools (AIT) in either a single borehole (such as FIG. 2A and/or 2B, or in two boreholes as shown in FIGS. 6 and 7.

Also shown in FIG. 7 is related surface equipment, according to some embodiments. Sources 702 are deployed in well 630 on a tool string suspended from a wireline cable 764 from logging truck 762. Logging truck 762 also is used to control the sources 702 and in communication with a processing center 750. Similarly receivers 708 are deployed in well 634 on a tool string suspended from a wireline cable 774 from logging truck 772. Measurements from receivers 708 are recorded and can be processed in one of the logging trucks 762 or 772 or can be transmitted directly to a processing center 750. Processing center 750 includes one or more central processing units 744 for carrying out the inversion procedures as described herein, as well as other processing. Processing center 750 also includes a storage system 742, communications and input/output modules 740, a user display 746 and a user input system 748. According to some embodiments, processing center 750 can be included in one or both of the logging trucks 762 and 772, or may be located in a location remote from the wellsites. Also shown in FIG. 7 is a surface electromagnetic array 780 for obtaining electromagnetic data. Thus the electromagnetic data used in the inversion procedures described herein can be obtained using various arrangements of equipment including single well (as in FIGS. 2A and 2B), cross well, surface to borehole, borehole to surface and surface to surface. Although wireline logging trucks are shown deploying the sources and receivers in FIG. 7, when deployed in a marine environment the sources and receivers may be deployed from a platform or vessel as well known in the art. Furthermore, according to other embodiments the sources and/or receivers can be deployed on a drill collar during part of a drilling operation. In the case of surface deployed electromagnetic arrays in the marine environment, according to some embodiments, surface array 780 can be implemented using deep-towed electric dipole antenna such as used with Controlled Source Electromagnetics (CSEM) surveys from WesterGeco, a business unit of Schlumbeger.

Figure 8A:
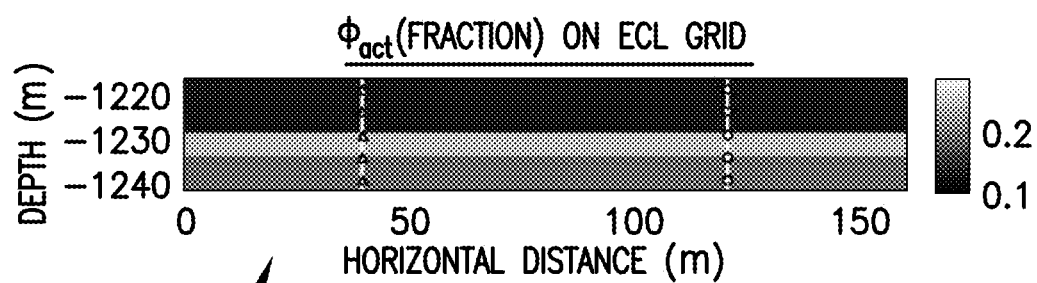
FIGS. 8A-H are vertical cross-sections of spatial distributions of the porosity, the conductivity, the water saturation and the salt concentration, according to some embodiments.
Figure 8B:
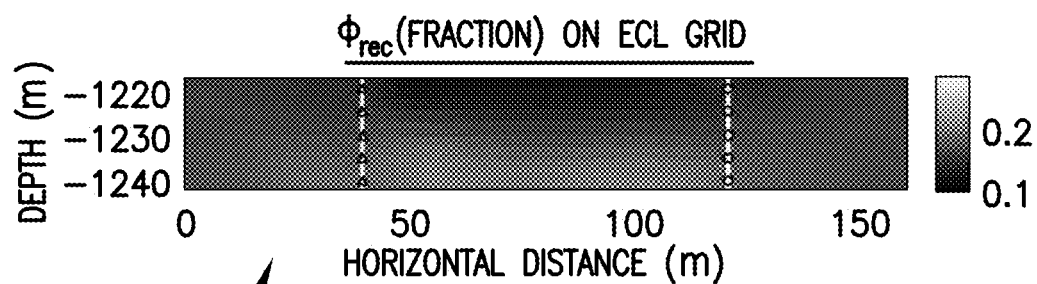
Figure 8C:
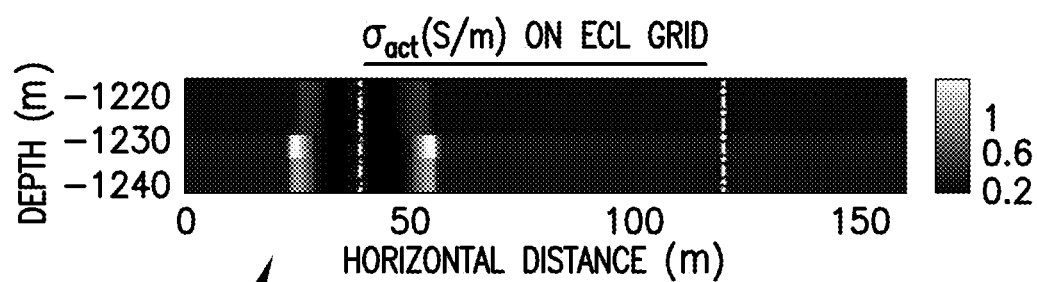
Figure 8D:
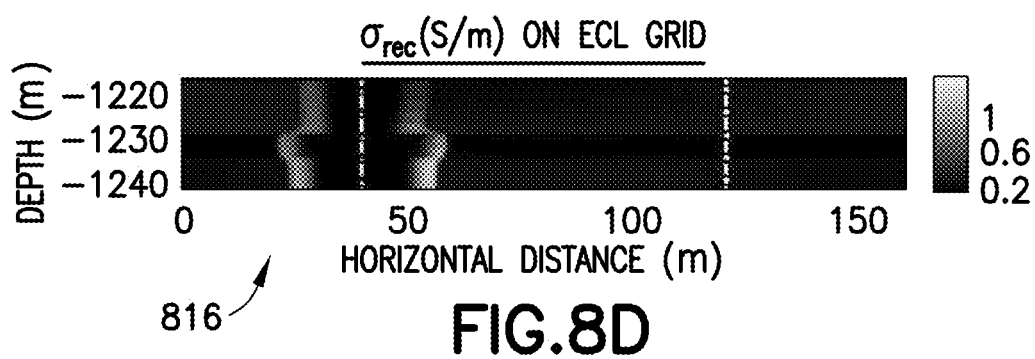
Figure 8E:
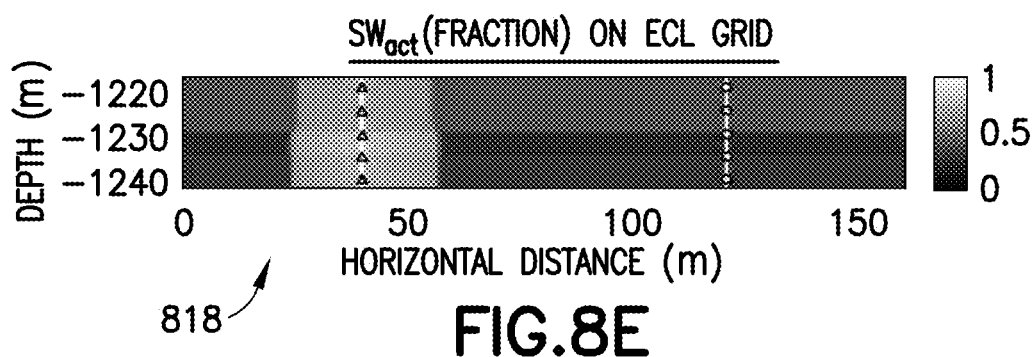
Figure 8F:
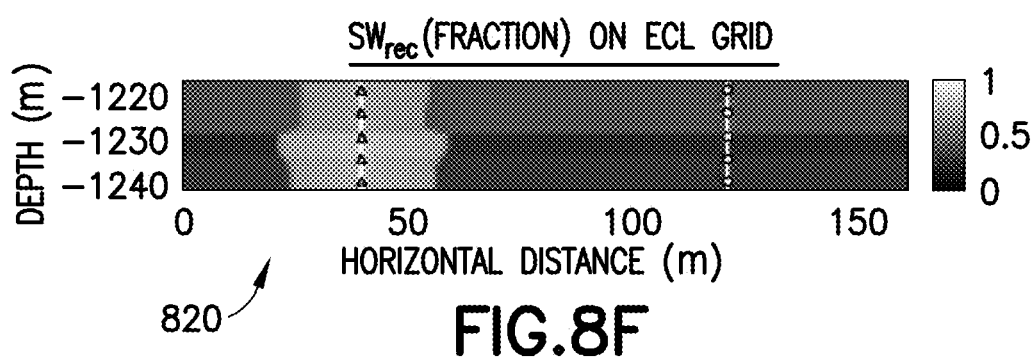
Figure 8G:
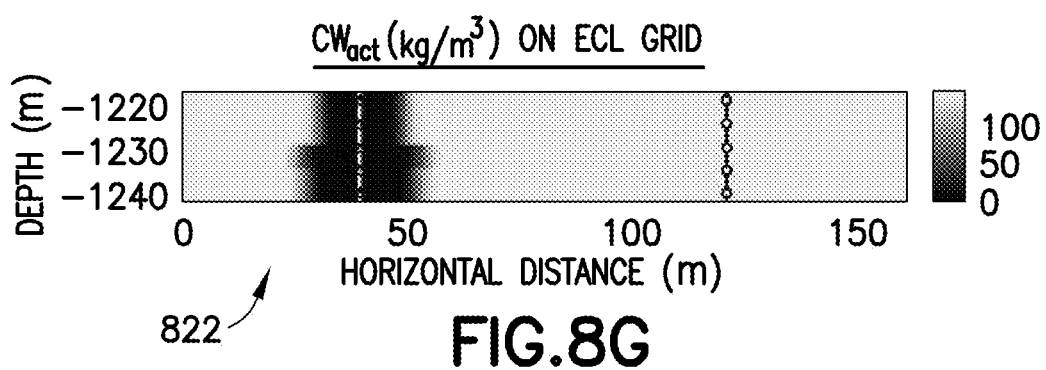
Figure 8H:
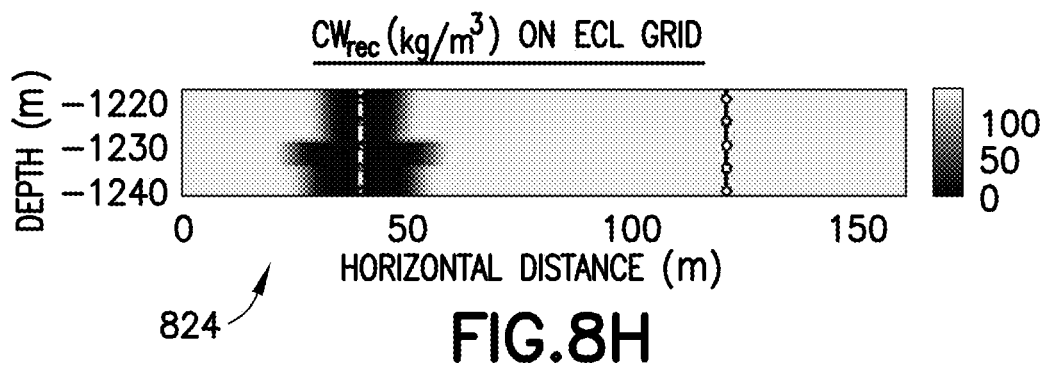

Because the crosswell electromagnetic inversion is not very sensitive to permeability, we assume the formation permeabilities are acquired from other independent measurements. FIGS. 8A-H are vertical cross-sections of spatial distributions of the porosity, the conductivity, the water saturation and the salt concentration, according to some embodiments. In FIG. 8A diagram 810 shows the true distribution of porosity, while in FIG. 8B diagram 812 shows the inverted distribution of porosity. In FIG. 8C, diagram 814 shows the true distribution for conductivity, while in FIG. 8D diagram 816 shows the reconstructed distribution for conductivity. In FIG. 8E, diagram 818 shows the true distribution for water saturation while in FIG. 8F, diagram 820 shows the reconstructed distribution for water saturation. In FIG. 8G, diagram 822 shows the true distribution for salt concentration, while in FIG. 8H, diagram 824 shows the reconstructed distribution for salt concentration. In all cases the data is corrupted with 2% Gauss random noise in the inversion. Compared to the true distribution, also as shown in FIG. 8, the inverted porosity recovers the true distribution to some extent. However, the reconstructed conductivity and water saturation are very close to the true distributions, and from which we can clearly see the fluid front, which is the main interest for the fluid movement monitoring.

According to some embodiments, a second example was conducted composed of 20 dipping layers, which were categorized into 4 rock types. Each rock type had different properties such as permeability, porosity and relative permeability. Similar to the example shown in FIGS. 6 and 7, water was simultaneously injected and oil produced in certain zones. It was assumed that the injection well was operated under bottomhole pressure control and the production well produces a constant oil rate. The same inversion procedure was implemented with additional 2% Gauss random noise added to the data. The spatial porosity distribution was recovered to some extent, and the water front was clearly seen from the reconstructed conductivity distribution.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method of estimating fluid invasion rate for portions of a subterranean formation of interest surrounding a borehole, the method comprising:
   generating electromagnetic signals within the subterranean formation of interest using at least one electromagnetic transmitter;
   detecting the generated electromagnetic signals using at least one electromagnetic receiver to obtain electromagnetic survey data of the subterranean formation of interest, wherein the electromagnetic survey data is representative of an electrical property of the subterranean formation of interest;
   directly inverting the electromagnetic survey data for a fluid invasion rate of a fluid, wherein the inversion is constrained by a fluid flow simulator that simulates a fluid flow process through the formation of interest and that generates simulated fluid flow characteristics; and
   generating an estimate of the fluid invasion rate based at least in part on the inversion.

2. A method according to claim 1 wherein the fluid is mud filtrate and the fluid invasion rate is a mud filtrate invasion rate.

3. A method according to claim 1 wherein the fluid is a well completion fluid and the fluid invasion rate is a completion fluid invasion rate.

4. A method according to claim 1 wherein the fluid is an injection fluid and the fluid invasion rate is a fluid injection rate.

5. A method according to claim 1 wherein the generated estimate of the fluid invasion rate is an average fluid invasion rate over a depth interval within the formation of interest.

6. A method according to claim 1 wherein the generated estimate of the fluid invasion rate is an average fluid invasion rate over a geologic bed within the formation of interest.

7. A method according to claim 1 further comprising receiving measured fluid flow characteristics relating to the formation of interest, wherein the measured fluid flow characteristics are generated from measurements made in the borehole and the direct inversion is a joint inversion of the electromagnetic survey data and the measured fluid flow characteristics.

8. A method according to claim 1 further comprising estimating porosity within the formation based at least in part on the inversion.

9. A method according to claim 1 further comprising generating a quantitative predictive formation model for at least part of the formation of interest based at least in part on the inversion.

10. A method according to claim 1, wherein the simulated fluid flow characteristics comprise spatial distributions of water saturation and salt concentration within the formation of interest.

11. The method of claim 1, wherein the at least one transmitter is deployed in the borehole and the at least one receiver is deployed in the borehole.

12. The method of claim 1, wherein the at least one transmitter is deployed in the borehole and the at least one receiver is deployed in a second borehole.

13. The method of claim 1, wherein the at least one transmitter is deployed at a surface location and the at least one receiver is deployed at a surface location.

14. The method of claim 1, wherein the at least one transmitter is deployed at a surface location and the at least one receiver is deployed in borehole.

15. The method of claim 1, wherein the at least one transmitter is deployed in a borehole and the at least one receiver is deployed at a surface location.

16. A method according to claim 7 further comprising estimating permeability within the formation based at least in part on the joint inversion.

17. A method according to claim 8 wherein the estimated porosity has a spatial resolution such that two or more values for porosity are estimated within one geologic bed.

18. A method according to claim 9 further comprising predicting future fluid flow in at least part of the formation of interest, the prediction being based at least in part on the generated quantitative predictive formation model.

19. A method according to claim 10 further comprising generating a conductivity distribution within the formation of interest using the spatial distributions of water saturation and salt concentration within the formation of interest.

20. A method according to claim 17 wherein the estimated porosity has a spatial resolution such that at least two porosity values are estimated within a predefined depth interval.

21. A method according to claim 19 further comprising generating simulated electromagnetic data from an electromagnetic simulator using the conductivity distribution within the formation of interest.

22. A fluid invasion rate estimation system that estimates fluid invasion rate for portions of a subterranean formation of interest surrounding a borehole, the system comprising:
    at least one electromagnetic transmitter configured to generate electromagnetic signals within the subterranean formation of interest;
    at least one electromagnetic receiver configured to detect the generated electromagnetic signals and to obtain electromagnetic survey data of the subterranean formation of interest, wherein the electromagnetic survey data is representative of an electrical property of the subterranean formation of interest;
    a processor; and
    a memory including instructions, that when executed by the processor, cause the fluid invasion rate system to:
    directly invert the electromagnetic survey data for a fluid invasion rate, wherein the inversion is constrained by a fluid flow simulator that simulates a fluid flow process through the formation of interest and that generates simulated fluid flow characteristics; and
    generate an estimate of the fluid invasion rate based at least in part on the inversion.

23. The fluid invasion rate estimation system of claim 22, wherein
    the direct inversion is a joint inversion of the electromagnetic survey data and measured fluid flow characteristics.

* * * * *